(12) United States Patent
Kaur et al.

(10) Patent No.: US 11,754,927 B2
(45) Date of Patent: Sep. 12, 2023

(54) PHOTORESIST PATTERN TRIMMING COMPOSITIONS AND PATTERN FORMATION METHODS

(71) Applicant: Rohm and Haas Electronic Materials LLC, Marlborough, MA (US)

(72) Inventors: Irvinder Kaur, Northborough, MA (US); Colin Liu, Shrewsbury, MA (US); Xisen Hou, Lebanon, NH (US); Kevin Rowell, Salem, MA (US); Mingqi Li, Shrewsbury, MA (US); Cheng-Bai Xu, Southborough, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 338 days.

(21) Appl. No.: 16/871,228

(22) Filed: May 11, 2020

(65) Prior Publication Data

US 2020/0379353 A1 Dec. 3, 2020

Related U.S. Application Data

(60) Provisional application No. 62/855,909, filed on May 31, 2019.

(51) Int. Cl.
*G03F 7/38* (2006.01)
*G03F 7/40* (2006.01)
(Continued)

(52) U.S. Cl.
CPC .............. *G03F 7/38* (2013.01); *C07C 309/01* (2013.01); *C07C 309/28* (2013.01);
(Continued)

(58) Field of Classification Search
None
See application file for complete search history.

(56) References Cited

U.S. PATENT DOCUMENTS

| | | | |
|---|---|---|---|
| 6,180,320 | B1 | 1/2001 | Saito et al. |
| 6,492,075 | B1 | 12/2002 | Templeton et al. |

(Continued)

FOREIGN PATENT DOCUMENTS

| | | |
|---|---|---|
| CN | 1531018 A | 9/2004 |
| JP | 2002006512 A | 1/2002 |

(Continued)

OTHER PUBLICATIONS

Search Report in corresponding Taiwan Application No. 109116370 dated Feb. 26, 2021.

*Primary Examiner* — Jiong-Ping Lu
(74) *Attorney, Agent, or Firm* — Jonathan D. Baskin

(57) ABSTRACT

Photoresist pattern trimming compositions comprise a polymer, an aromatic sulfonic acid, and an organic-based solvent system, wherein the aromatic sulfonic acid is of general formula (I):

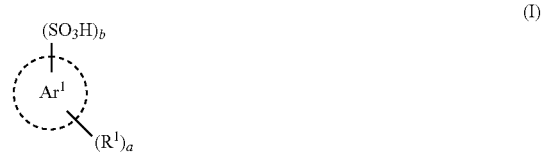

wherein: $Ar^1$ represents an aromatic group; $R^1$ independently represents a halogen atom, hydroxy, substituted or unsubstituted alkyl, substituted or unsubstituted heteroalkyl, substituted or unsubstituted carbocyclic aryl, substituted or
(Continued)

unsubstituted heterocyclic aryl, substituted or unsubstituted alkoxy, or a combination thereof, wherein adjacent $R^1$ groups together optionally form a fused ring structure with $Ar^1$; a represents an integer of 2 or more; and b represents an integer of 1 or more, provided that a+b is at least 3 and is not greater than the total number of available aromatic carbon atoms of $Ar^1$, and two or more of $R^1$ are independently a fluorine atom or a fluoroalkyl group bonded directly to an aromatic ring carbon atom.

16 Claims, 1 Drawing Sheet

(51) Int. Cl.
*C07C 309/28* (2006.01)
*H01L 21/311* (2006.01)
*H01L 21/027* (2006.01)
*C07C 309/01* (2006.01)
*C07C 309/39* (2006.01)

(52) U.S. Cl.
CPC .............. *C07C 309/39* (2013.01); *G03F 7/40* (2013.01); *H01L 21/0273* (2013.01); *H01L 21/31138* (2013.01)

(56) References Cited

U.S. PATENT DOCUMENTS

| 7,338,750 | B2 | 3/2008 | Kozawa et al. |
| 9,760,011 | B1 | 9/2017 | Rowell et al. |
| 2003/0017711 | A1 | 1/2003 | Mahorowata et al. |
| 2009/0311490 | A1 | 12/2009 | Burns et al. |
| 2013/0171574 | A1 | 7/2013 | Xu |
| 2013/0171825 | A1 | 7/2013 | Xu |
| 2014/0186772 | A1 | 7/2014 | Pohlers et al. |
| 2016/0187783 | A1 | 6/2016 | Kaur et al. |
| 2017/0010535 | A1 | 6/2017 | Fujitani et al. |
| 2017/0255102 | A1* | 9/2017 | Rowell ............... G03F 7/30 |

FOREIGN PATENT DOCUMENTS

| JP | 2002299202 | A | 10/2002 |
| JP | 2005-091427 | A | 4/2005 |
| JP | 04329216 | B2 | 9/2009 |
| JP | 2013218191 | A | 10/2013 |

\* cited by examiner

PHOTORESIST PATTERN TRIMMING COMPOSITIONS AND PATTERN FORMATION METHODS

BACKGROUND

The invention relates generally to the manufacture of electronic devices. More specifically, this invention relates to photoresist pattern trimming compositions and to pattern formation methods using such compositions. The compositions and methods find particular use in the formation of fine lithographic patterns.

In the semiconductor manufacturing industry, photoresist materials are used for transferring an image to one or more underlying layers, such as metal, semiconductor or dielectric layers, disposed on a semiconductor substrate, as well as to the substrate itself. To increase the integration density of semiconductor devices and allow for the formation of structures having dimensions in the nanometer range, photoresists and photolithography processing tools having high-resolution capabilities have been and continue to be developed.

Positive-tone chemically amplified photoresists are conventionally used for high-resolution processing. Such resists typically employ a resin having acid-labile leaving groups and a photoacid generator. Patternwise exposure to activating radiation through a photomask causes the acid generator to form an acid which, during post-exposure baking, causes cleavage of the acid-labile groups in exposed regions of the resin. This creates a difference in solubility characteristics between exposed and unexposed regions of the resist in an aqueous alkaline developer solution. In a positive tone development (PTD) process, exposed regions of the resist are soluble in the aqueous alkaline developer and are removed from the substrate surface, whereas unexposed regions, which are insoluble in the developer, remain after development to form a positive image.

Lithographic scaling has conventionally been achieved by increasing the numerical aperture of optical exposure tools and by use of shorter exposure wavelengths. To form finer photoresist patterns than attainable by direct imaging alone, photoresist pattern trimming processes have been proposed, for example, in U.S. Patent Application Publication Nos. US20130171574A1, US20130171825A1, US2014/0186772A1 and US2016/0187783A1. Photoresist trimming processes typically involve contacting a photoresist pattern that includes a polymer having acid labile groups with a composition containing an acid or thermal acid generator. The acid or generated acid causes deprotection in a surface region of the resist pattern, which region is then removed, for example, by contact with a developer solution. This allows for trimming of the photoresist pattern, resulting, for example, in the creation of finer resist line or pillar patterns than when using direct imaging alone. With reductions in pattern size and device geometry, however, trimming process considerations such as linewidth roughness, pattern collapse margin, and coating defect levels, are becoming of increased importance for minimizing defects which can adversely impact performance and/or yield of resulting electronic devices.

There is a need in the art for photoresist pattern trimming compositions and pattern formation methods useful in electronic device fabrication that address one or more problems associated with the state of the art.

SUMMARY OF THE INVENTION

In accordance with a first aspect of the invention, pattern trimming compositions are provided. The compositions comprise a polymer, an aromatic sulfonic acid, and an organic-based solvent system, wherein the aromatic sulfonic acid is of general formula (I):

wherein: $Ar^1$ represents an aromatic group; $R^1$ independently represents a halogen atom, hydroxy, substituted or unsubstituted alkyl, substituted or unsubstituted heteroalkyl, substituted or unsubstituted carbocyclic aryl, substituted or unsubstituted heterocyclic aryl, substituted or unsubstituted alkoxy, or a combination thereof, wherein adjacent $R^1$ groups together optionally form a fused ring structure with $Ar^1$; a represents an integer of 2 or more; and b represents an integer of 1 or more, provided that a+b is at least 3 and is not greater than the total number of available aromatic carbon atoms of $Ar^1$, and two or more of $R^1$ are independently a fluorine atom or a fluoroalkyl group bonded directly to an aromatic ring carbon atom.

Also provided are pattern formation methods. The methods comprise: (a) providing a semiconductor substrate; (b) forming a photoresist pattern over the semiconductor substrate, wherein the photoresist pattern is formed from a photoresist composition comprising: a polymer comprising acid labile groups; and a photoacid generator; (c) coating a pattern trimming composition as described herein over the photoresist pattern; (d) heating the coated photoresist pattern; and (e) rinsing the coated and heated photoresist pattern with a rinsing agent to remove residual pattern treatment composition. Preferable methods and compositions of the invention can provide photoresist patterns having desired characteristics, for example, one or more characteristics including change in critical dimension (ΔCD), linewidth roughness (LWR), pattern collapse margin (PCM) or coating defectivity.

The terminology used herein is for the purpose of describing particular embodiments only and is not intended to be limiting of the invention. The singular forms "a", "an" and "the" are intended to include singular and plural forms, unless the context indicates otherwise.

DESCRIPTION OF THE DRAWINGS

The present invention will be described with reference to the following drawing, in which like reference numerals denote like features, and in which.

DETAILED DESCRIPTION

Photoresist Pattern Trimming Compositions

Figure 1A:
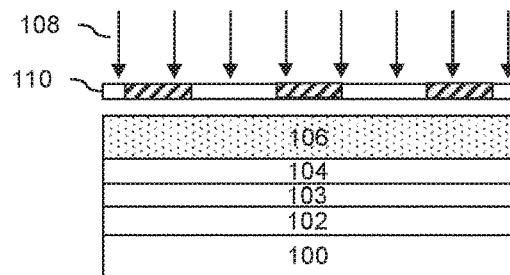
FIG. 1A-H illustrates an exemplary process flow for forming a pattern in accordance with the invention.

Photoresist pattern trimming compositions of the invention include a polymer, an aromatic sulfonic acid, and an organic-based solvent, and can include one or more optional additional components. The polymer allows for the compositions to be coated over the photoresist pattern in the form of a layer having a desired thickness. The polymer should have good solubility in the rinsing agent to be used in the patterning process. For example, the polymer can be soluble in an aqueous alkaline solution such as those typically used as photoresist developers, preferably aqueous quaternary ammonium hydroxide solutions such as aqueous tetramethylammonium hydroxide (TMAH) (e.g., a 0.26N TMAH) solutions. To minimize residue defects originating from the pattern trimming composition, the dissolution rate of a dried layer of the trimming composition in a rinsing agent to be applied should be greater than that of the photoresist pattern in the rinsing agent. The polymer typically exhibits a dissolution rate in the rinsing agent, preferably a 0.26N TMAH solution, of 100 Å/second or higher, preferably 1000 Å/second or higher. The polymer should be soluble in the solvent system of the trimming composition.

The polymer can be formed from one or more monomers chosen, for example, from those having an ethylenically unsaturated polymerizable double bond, such as: (meth)acrylate monomers such as isopropyl(meth)acrylate and n-butyl(meth)acrylate; (meth)acrylic acid; vinyl aromatic monomers such as styrene, hydroxystyrene, vinyl naphthalene and acenaphthylene; vinyl alcohol; vinyl chloride; vinyl pyrrolidone; vinyl pyridine; vinyl amine; vinyl acetal; and combinations thereof. The polymer preferably includes one or more repeat units formed from vinyl aromatic monomers. Preferably, the polymer contains one or more functional groups chosen, for example, from hydroxy, acid groups such as carboxyl, sulfonic acid and sulfonamide, silanol, fluoroalcohol such as hexafluoroisopropyl alcohol [—C(CF$_3$)$_2$OH], anhydrates, lactones, esters, ethers, allylamine, pyrrolidones and combinations thereof. Of these, —C(CF$_3$)$_2$OH and acid groups such as carboxyl, sulfonic acid and sulfonamide are particularly preferred. The polymer can be a homopolymer or a copolymer having a plurality of distinct repeat units, for example, two, three, four or more distinct repeat units. In one aspect, the repeat units of the polymer are all formed from (meth)acrylate monomers, are all formed from (vinyl)aromatic monomers or are all formed from (meth)acrylate monomers and (vinyl) aromatic monomers. When the polymer includes more than one type of repeat unit, it typically takes the form of a random copolymer.

Suitable polymers in accordance with the invention include, for example, the following:

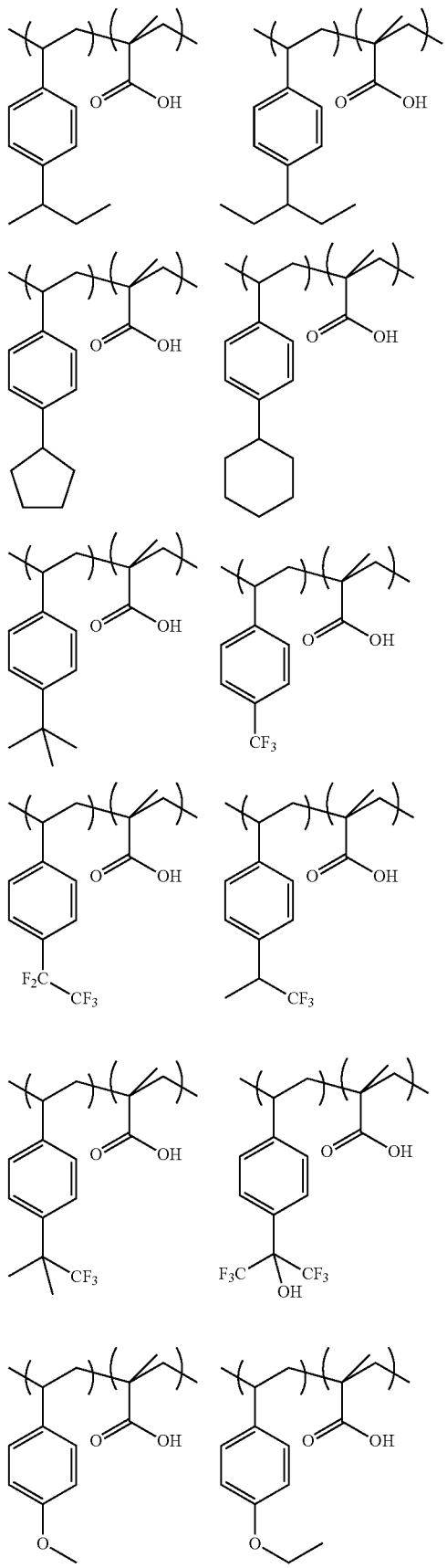

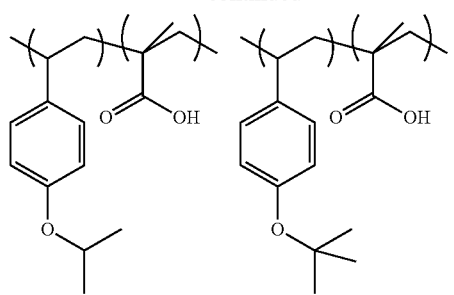
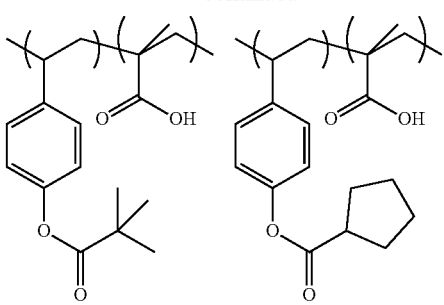
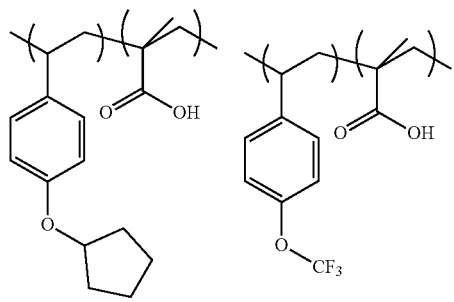
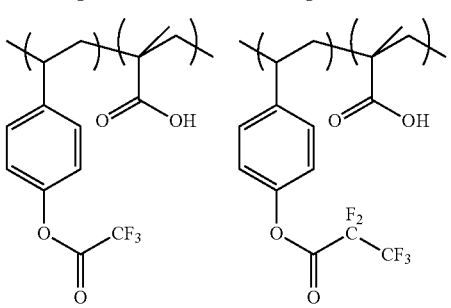
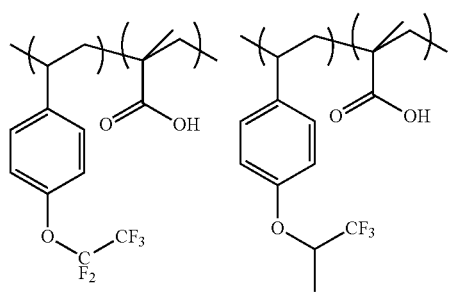
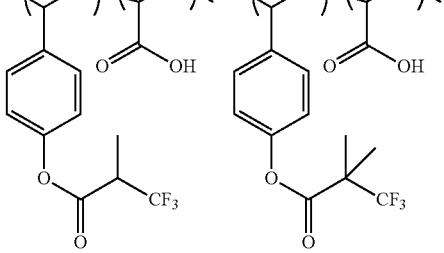
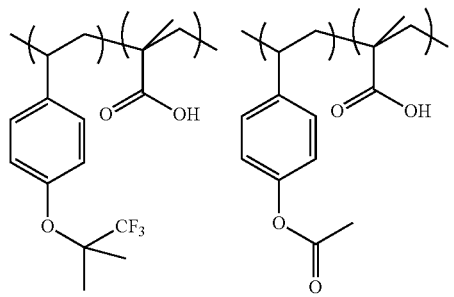
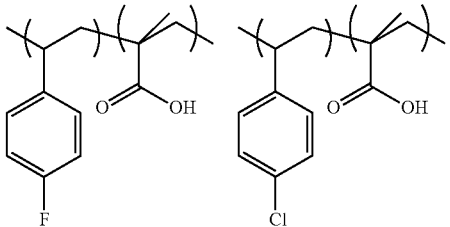
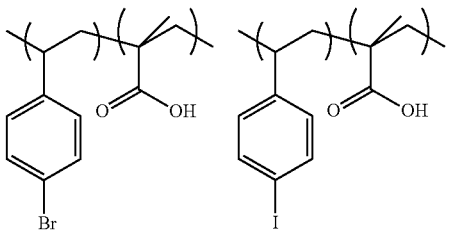
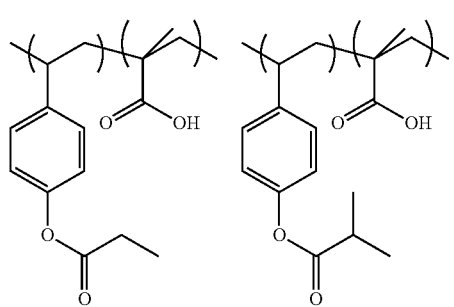
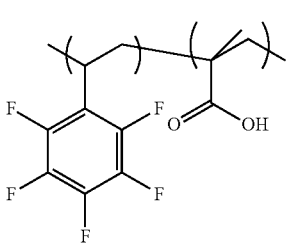

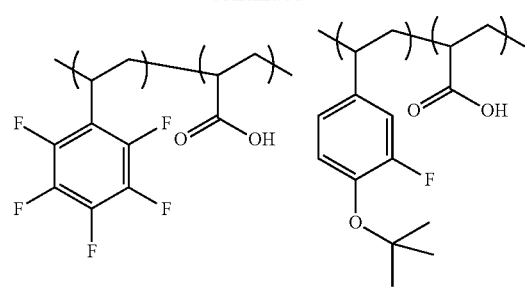
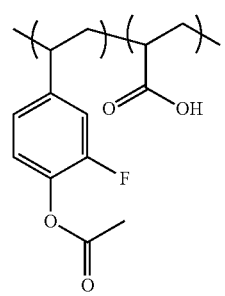
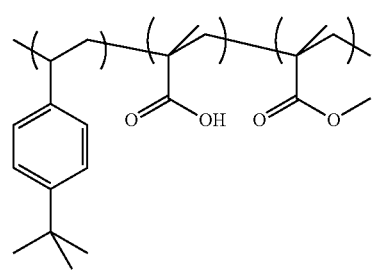
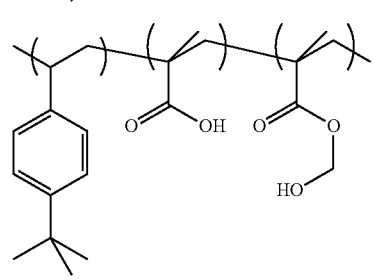
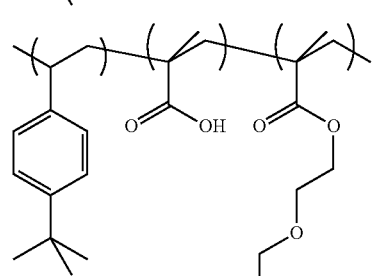
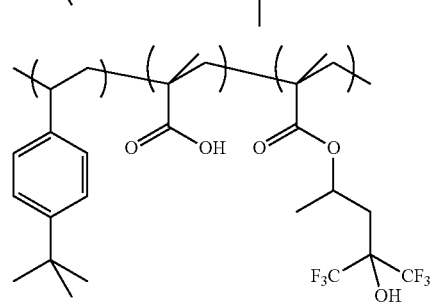
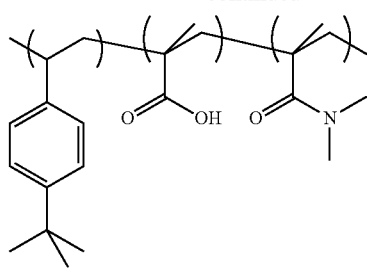
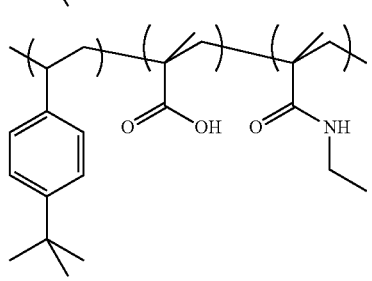
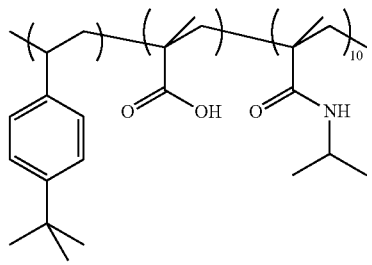
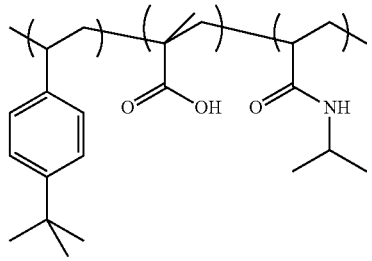
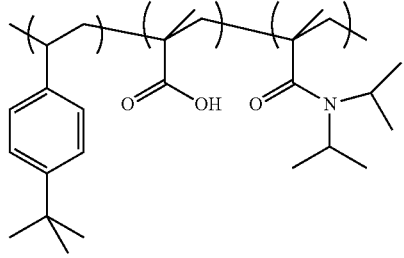
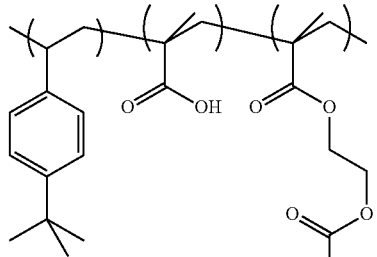

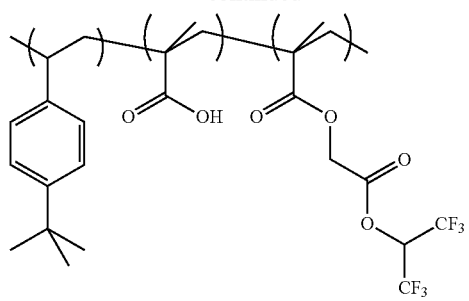
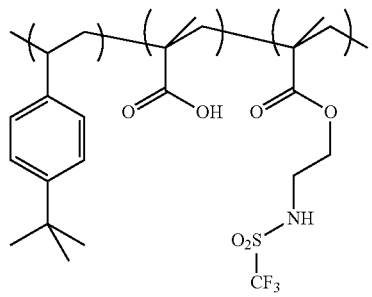
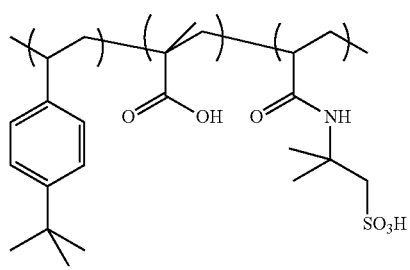
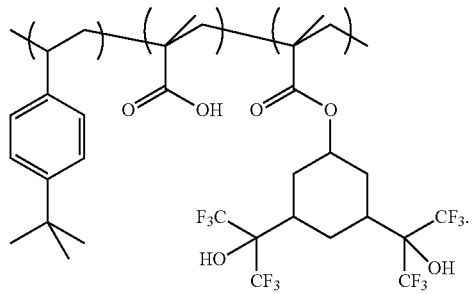
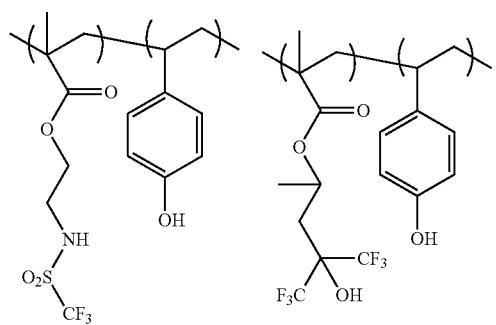
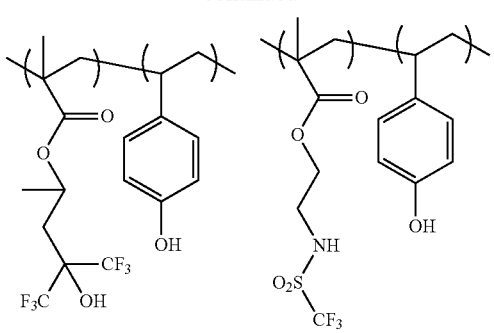
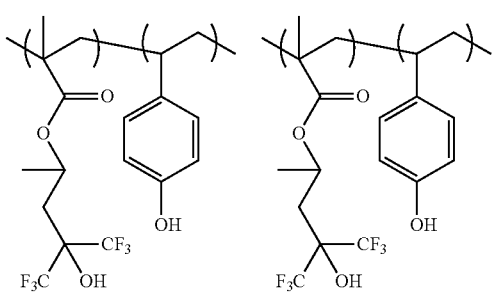
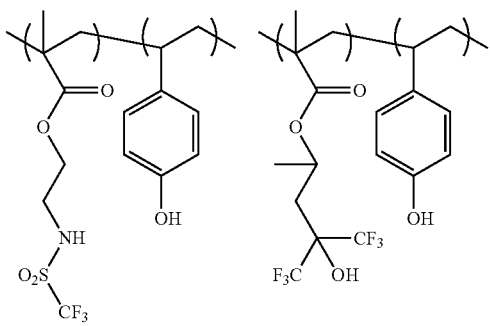
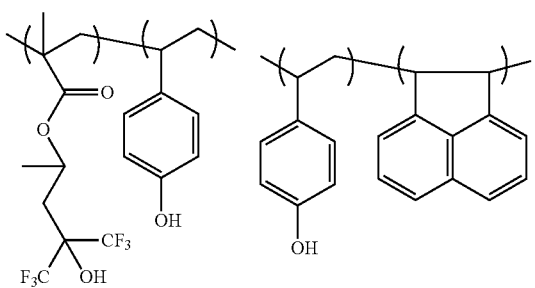
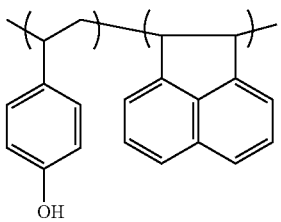
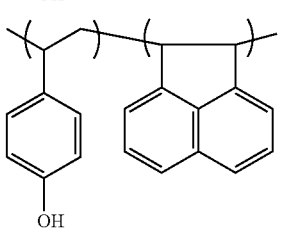

-continued
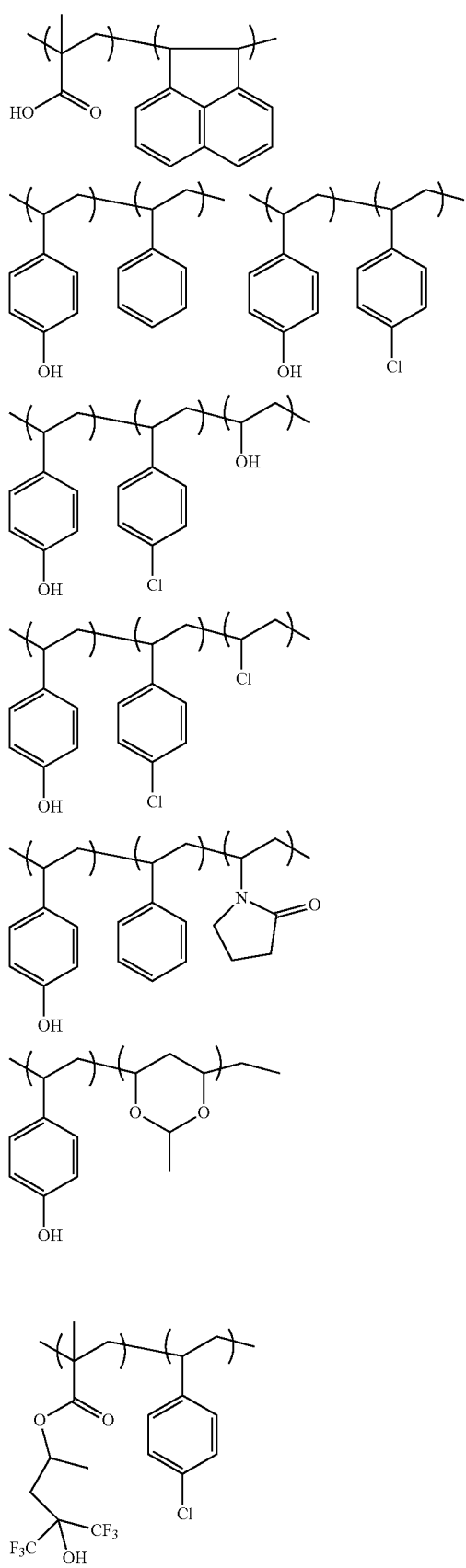
-continued
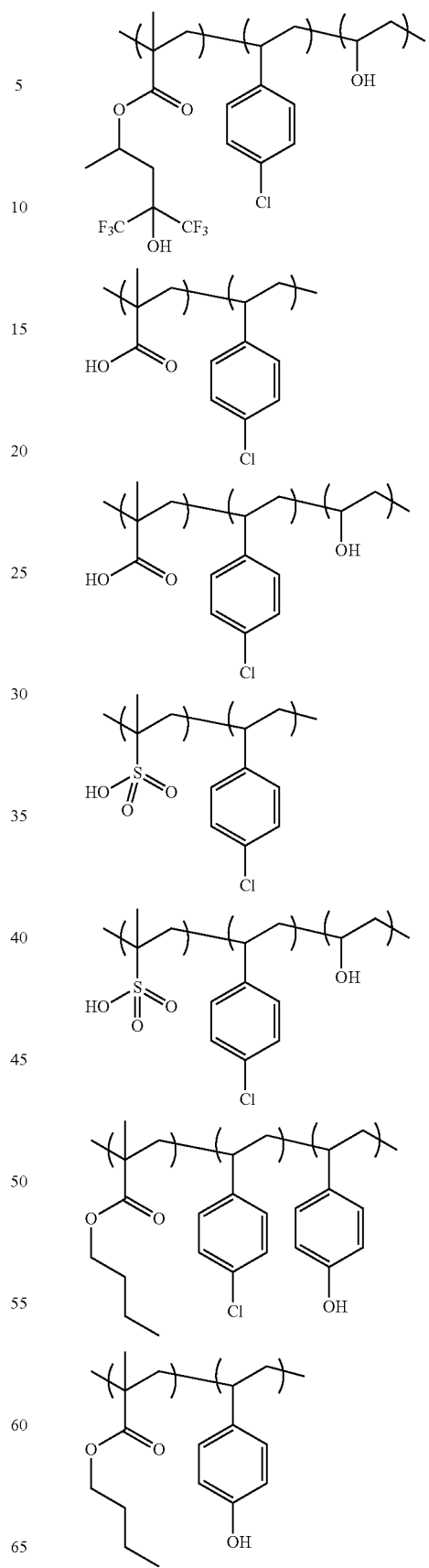

-continued

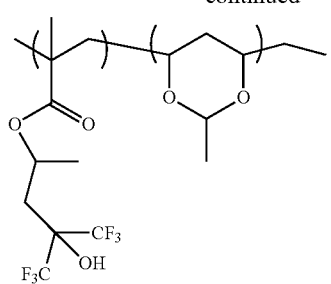
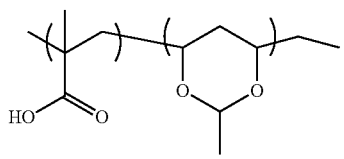
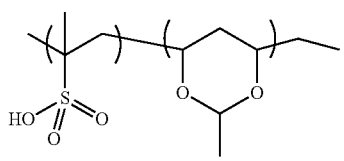
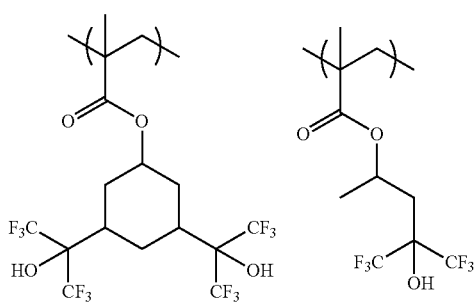
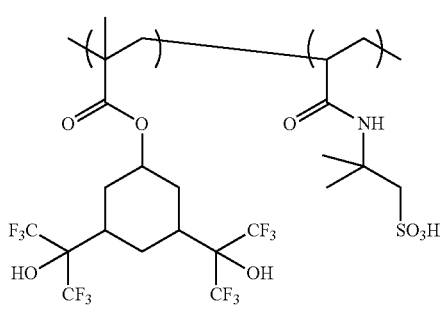
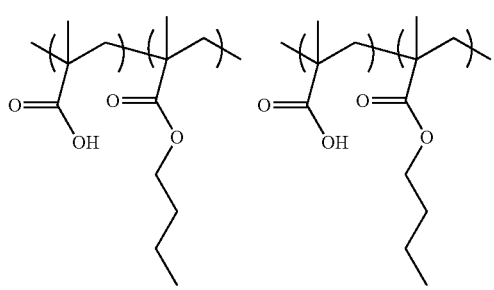

-continued

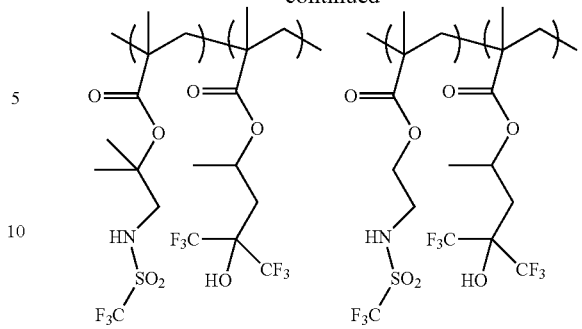
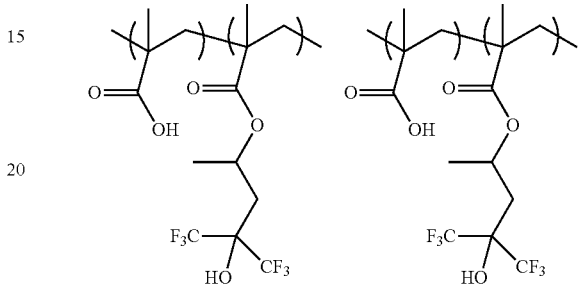
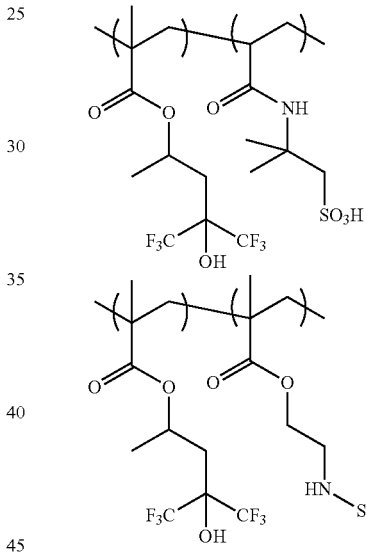

The trimming compositions typically include a single polymer, but can optionally include one or more additional polymers. The content of the polymer in the composition will depend, for example, on the target thickness of the layer, with a higher polymer content being used when thicker layer is desired. The polymer is typically present in the pattern trimming composition in an amount of from 80 to 99.9 wt %, more typically from 90 to 99 wt %, or 95 to 99 wt %, based on total solids of the trimming composition. The weight average molecular weight (Mw) of the polymer is typically less than 400,000, preferably from 3000 to 50,000, more preferably from 3000 to 25,000, as measured by GPC versus polystyrene standards. Typically, the polymer will have a polydispersity index (PDI=Mw/Mn) of 3 or less, preferably 2 or less, as measured by GPC versus polystyrene standards.

Suitable polymers for use in the trimming compositions are commercially available and/or can readily be made by persons skilled in the art. For example, the polymer may be synthesized by dissolving selected monomers corresponding to units of the polymer in an organic solvent, adding a radical polymerization initiator thereto, and effecting heat polymerization to form the polymer. Examples of suitable organic solvents that can be used for polymerization of the polymer include, for example, toluene, benzene, tetrahydrofuran, diethyl ether, dioxane, ethyl lactate and methyl isobutyl carbinol. Suitable polymerization initiators include, for example, 2,2'-azobisisobutyronitrile (AIBN), 2,2'-azobis (2,4-dimethylvaleronitrile), dimethyl 2,2-azobis(2-methylpropionate), benzoyl peroxide and lauroyl peroxide.

The trimming compositions further include an aromatic sulfonic acid that is non-polymeric. In the case of a photoresist based on deprotection reaction, the acid with heat can cause cleavage of the bonds of acid labile groups in a surface region of the photoresist pattern, causing increased solubility of the photoresist polymer in a rinsing solution to be applied.

The aromatic sulfonic acid is of general formula (I):

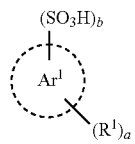

wherein $Ar^1$ represents an aromatic group, which may be carbocyclic, heterocyclic, or a combination thereof. The aromatic group may be monocyclic, for example, phenyl or pyridyl, or polycyclic, for example biphenyl, and can include fused aromatic rings such as naphthyl, anthracenyl, or pyrenyl or fused ring systems having both aromatic and non-aromatic rings such as 1,2,3,4-tetrahydronaphthalene, 9,10-dihydroanthracene or fluorene. The aromatic group typically has from 4 to 18 carbons, and preferably from 6 to 14 carbons. Suitable aromatic groups include, but are not limited to: phenyl, biphenyl, naphthalenyl, anthracenyl, phenanthrenyl, pyrenyl, tetracenyl, triphenylenyl, tetraphenyl, benzo[f]tetraphenyl, benzo[m]tetraphenyl, and benzo[k]tetraphenyl. Of these, phenyl is particularly preferred. $R^1$ independently represents a halogen atom, hydroxy, substituted or unsubstituted alkyl ($C_{1-12}$), substituted or unsubstituted heteroalkyl ($C_{1-12}$), substituted or unsubstituted carbocyclic aryl ($C_{6-12}$), substituted or unsubstituted heterocyclic aryl ($C_{4-12}$), substituted or unsubstituted alkoxy ($C_{1-12}$), or a combination thereof. Adjacent $R^1$ groups together may optionally form a fused ring structure with $Ar^1$. $R^1$ independently represents a fluorine atom or trifluoromethyl.

The alkyl and heteroalkyl groups can be linear, branched or cyclic in structure. The term "substituted" refers to a group having one or more of its hydrogen atoms replaced with one or more substituents selected from hydroxy, halogen, $C_{1-12}$ alkyl, $C_{1-12}$ heteroalkyl, $C_{1-12}$ alkoxy, $C_{6-12}$ aryl or $C_{4-12}$ heteroaryl.

a represents an integer of 2 or more, preferably an integer from 2 to 4, and more preferably 2, and b represents an integer of 1 or more, preferably an integer from 1 to 2, and more preferably 1, provided that a+b is at least 3 and is not greater than the total number of available aromatic carbon atoms of $Ar^1$. Typically, a+b is at from 3 to 5. Two or more of $R^1$ are independently a fluorine atom or a fluoroalkyl group bonded directly to an aromatic ring carbon atom. The fluoroalkyl group can be linear, branched or cyclic, and typically has from 1 to 12 carbon atoms, preferably from 1 to 6 carbon atoms, and more preferably 1 or 2 carbon atoms, with trifluoromethyl being typical. When branched or cyclic, $R^1$ will have a minimum of 3 carbon atoms. $R^1$ is at least partially fluorinated, and is preferably perfluorinated. The aromatic sulfonic acid is typically present in an amount of from about 0.01 to 20 wt % based on total solids of the trimming composition.

Preferably, the aromatic sulfonic acid is of general formula II:

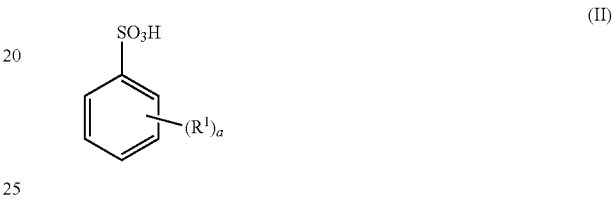

wherein: $R^1$ is as defined above; a represents an integer of from 2 to 5, and two or more of $R^1$ are independently a fluorine atom or a fluoroalkyl group.

Suitable exemplary aromatic sulfonic acids include the following:

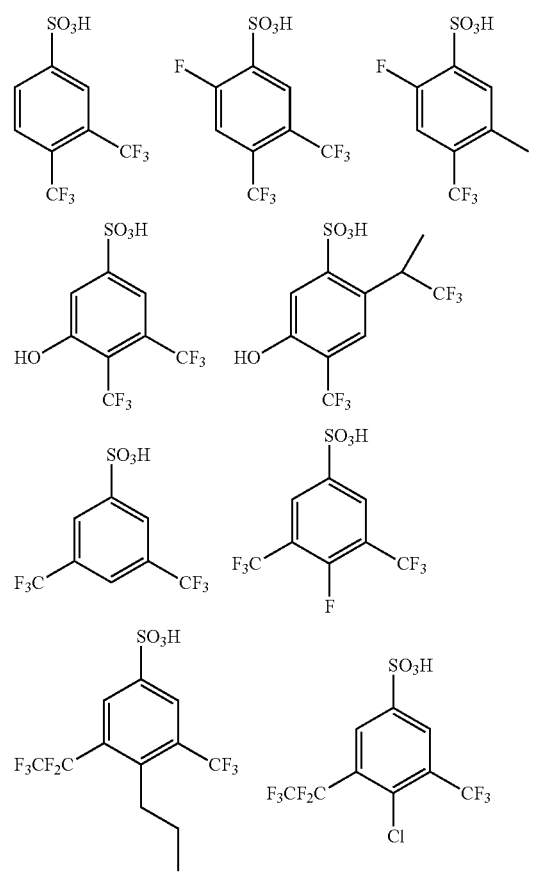

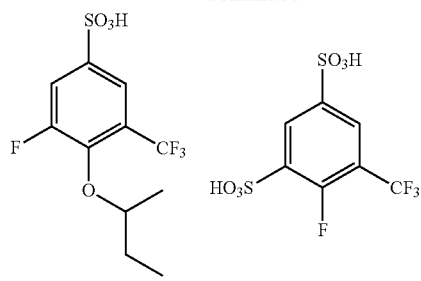
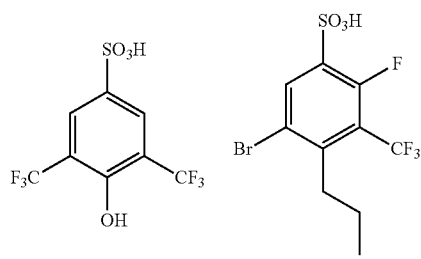
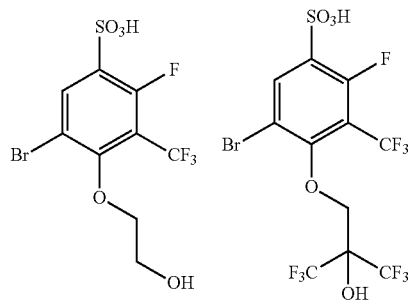
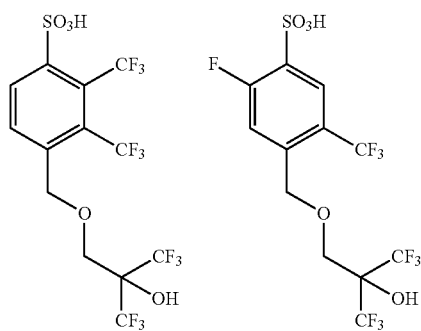
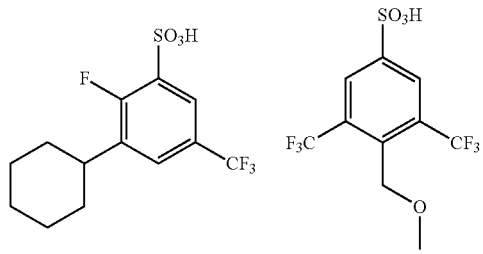
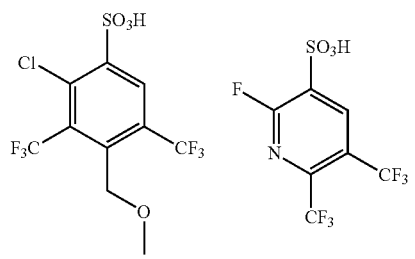
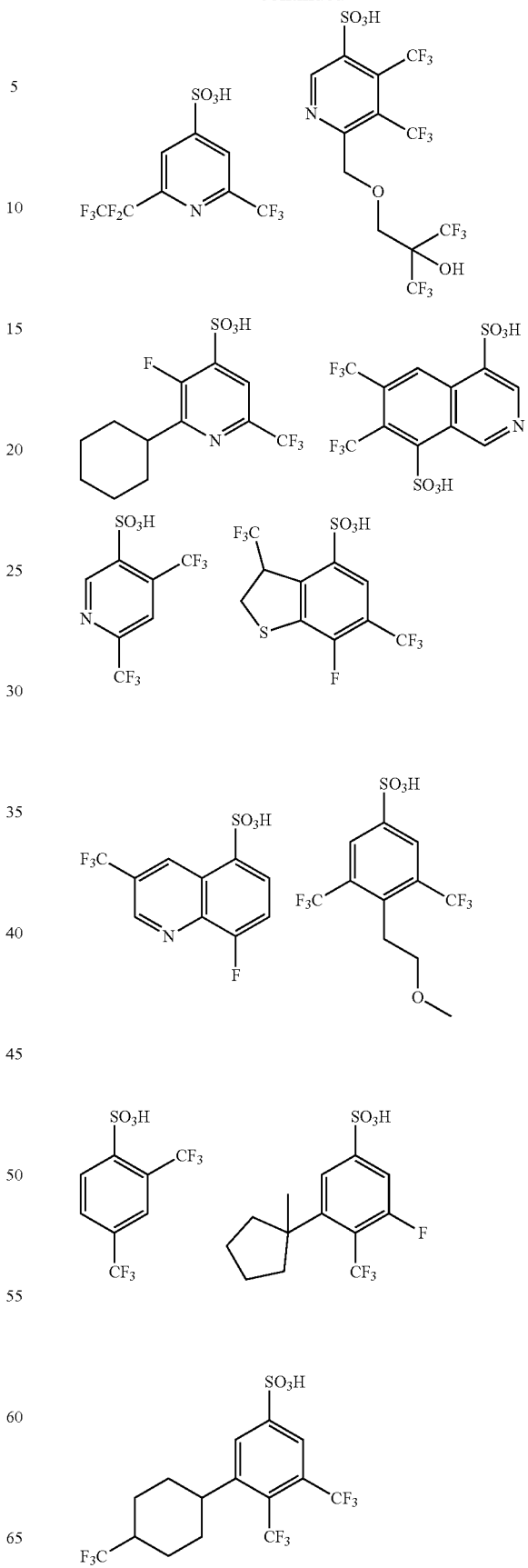

-continued
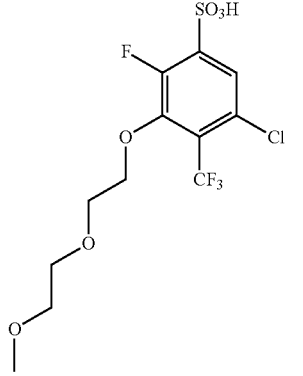
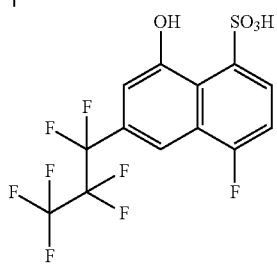
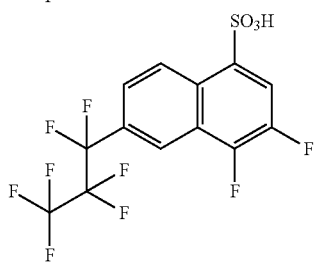
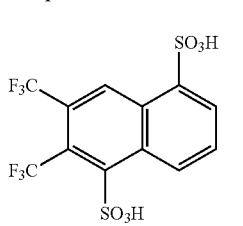
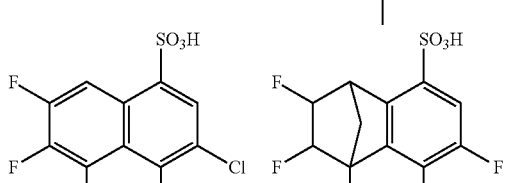
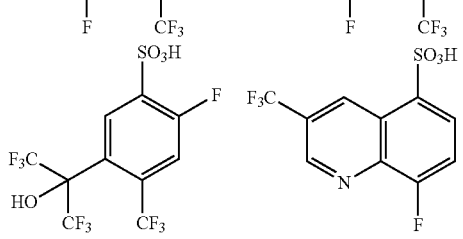
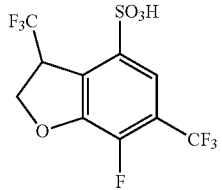
-continued
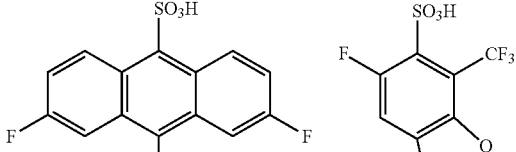
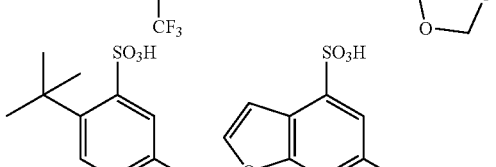
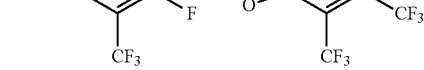
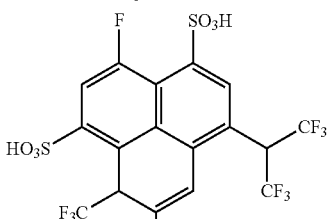
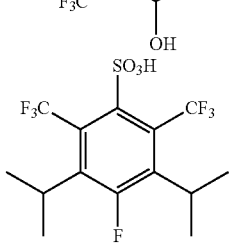
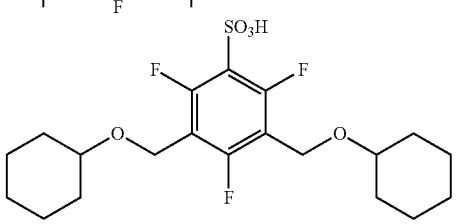
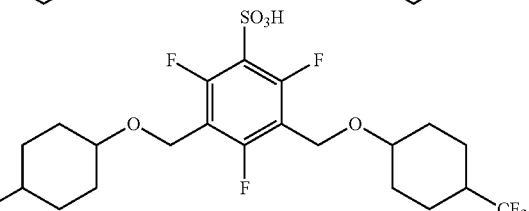
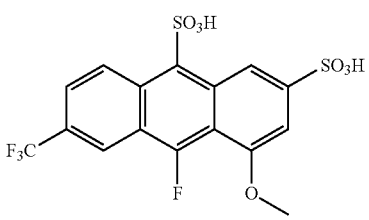
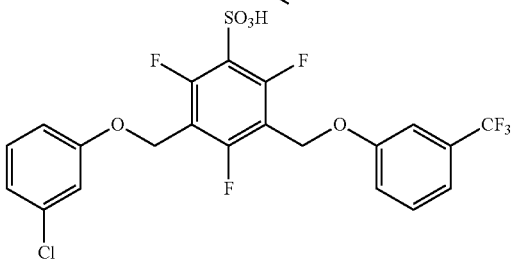

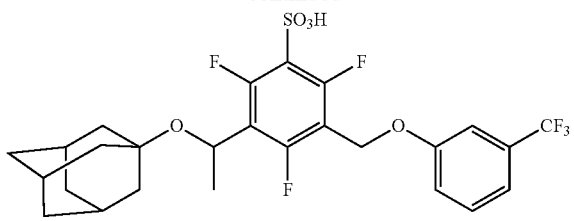
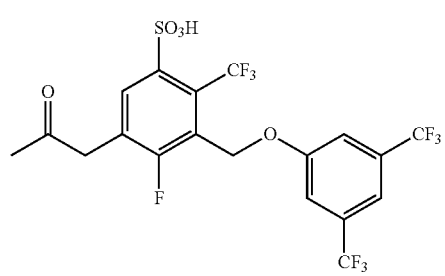
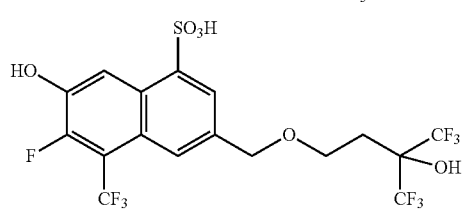
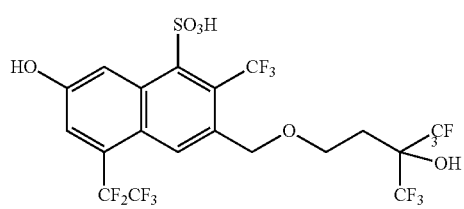
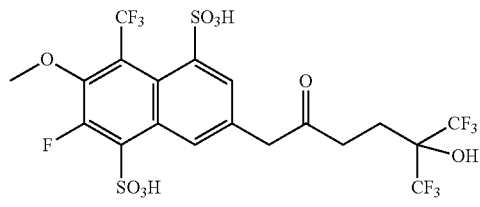
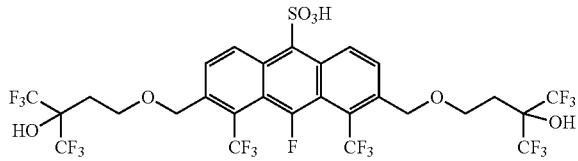
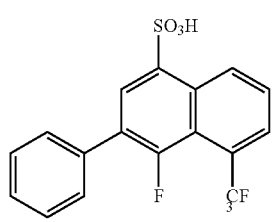
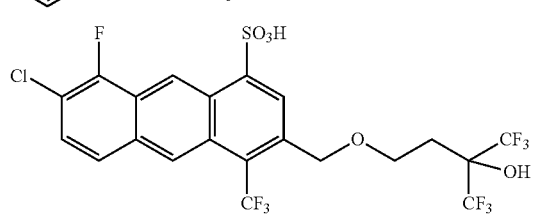
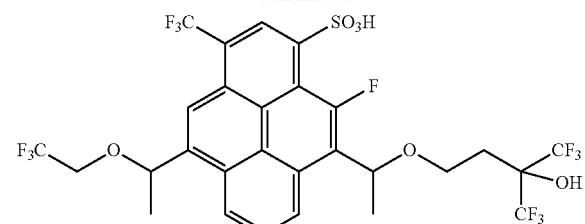
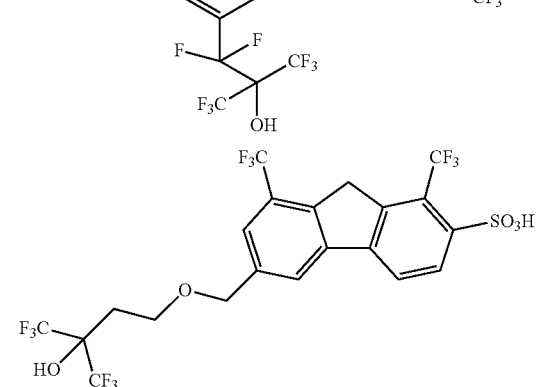
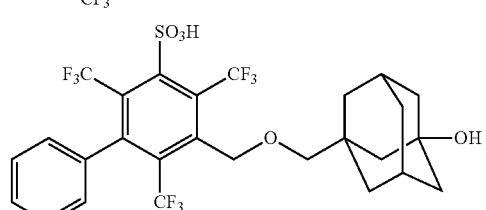
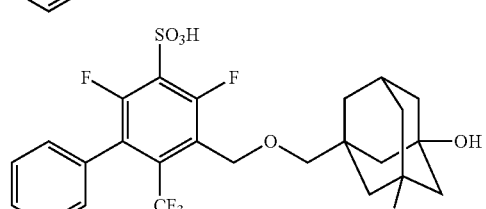
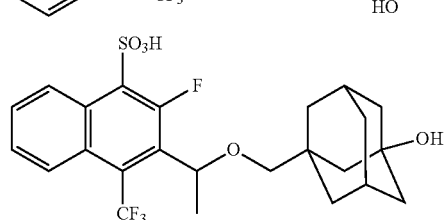
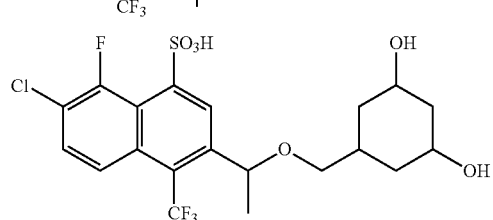
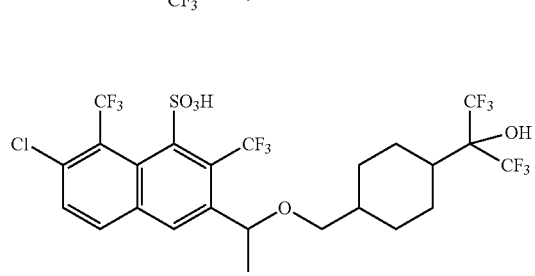

-continued

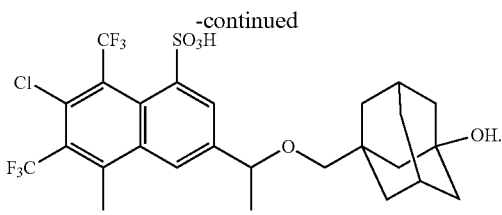

The trimming compositions further include an organic-based solvent system comprising one or more different solvents. The term "organic-based" means that the solvent system includes greater than 50 wt % organic solvent based on total solvents of the trimming composition, more typically greater than 90 wt %, greater than 95 wt %, greater than 99 wt % or 100 wt % organic solvents, based on total solvents of the trimming compositions. Suitable solvent materials to formulate and cast the trimming compositions should exhibit good solubility characteristics with respect to the non-solvent components of the trimming composition, without appreciably dissolving the underlying photoresist pattern, so as to minimize intermixing with the photoresist pattern.

Suitable organic solvents for the trimming composition include, for example: alkyl esters such as alkyl propionates, such as n-butyl propionate, n-pentyl propionate, n-hexyl propionate and n-heptyl propionate, and alkyl butyrates such as n-butyl butyrate, isobutyl butyrate and isobutyl isobutyrate; ketones such as 2,5-dimethyl-4-hexanone and 2,6-dimethyl-4-heptanone; aliphatic hydrocarbons such as n-heptane, n-nonane, n-octane, n-decane, 2-methylheptane, 3-methylheptane, 3,3-dimethylhexane and 2,3,4-trimethylpentane, and fluorinated aliphatic hydrocarbons such as perfluoroheptane; alcohols such as straight, branched or cyclic $C_4$-$C_9$ monohydric alcohol such as 1-butanol, 2-butanol, isobutyl alcohol, tert-butyl alcohol, 3-methyl-1-butanol, 1-pentanol, 2-pentanol, 4-methyl-2-pentanol, 1-hexanol, 1-heptanol, 1-octanol, 2-hexanol, 2-heptanol, 2-octanol, 3-hexanol, 3-heptanol, 3-octanol and 4-octanol; 2,2,3,3,4,4-hexafluoro-1-butanol, 2,2,3,3,4,4,5,5-octafluoro-1-pentanol and 2,2,3,3,4,4,5,5,6,6-decafluoro-1-hexanol, and $C_5$-$C_9$ fluorinated diols such as 2,2,3,3,4,4-hexafluoro-1,5-pentanediol, 2,2,3,3,4,4,5,5-octafluoro-1,6-hexanediol and 2,2,3,3,4,4,5,5,6,6,7,7-dodecafluoro-1,8-octanediol; ethers such as isopentyl ether and dipropylene glycol monomethyl ether; and mixtures containing one or more of these solvents.

When the photoresist pattern to be trimmed is formed from a vinyl aromatic-based polymer, such as a polymer containing styrene- and/or hydroxystyrene-units, the solvent system preferably comprises one or more monoether solvents. Use of a monoether-based solvent system can provide low toploss characteristics when treating vinyl aromatic-based photoresist patterns. As used herein, "vinyl aromatic" means polymerized units formed from monomers in which an aromatic group is bonded directly to a vinyl group, for example, styrene, hydroxystyrene and vinyl naphthalene. "Vinyl aromatic-based polymer" means that the polymer contains greater than 50 mol % vinyl aromatic units based on total units of the polymer, more typically from 50 to 90 mol % or from 60 to 80 mol %, based on total units of the polymer.

Suitable monoether-containing solvent systems comprise one or more monoether solvents in a combined amount of from 50 to 98 wt %, preferably 70 to 98 wt %, 80 to 98 wt % or 90 to 98 wt %, based on the solvent system. Preferred monoether solvents include alkyl monoethers and aromatic monoethers, particularly preferred of which are those having a total carbon number of from 6 to 16. Suitable alkyl monoethers include, for example, 1,4-cineole, 1,8-cineole, pinene oxide, di-n-propyl ether, diisopropyl ether, di-n-butyl ether, di-n-pentyl ether, diisoamyl ether, dihexyl ether, diheptyl ether and dioctyl ether, with diisoamyl ether being preferred. Suitable aromatic monoethers include, for example, anisole, ethylbenzyl ether, diphenyl ether, dibenzyl ether and phenetole, with anisole being preferred.

The ether-containing solvent system preferably further includes one or more alcohol and/or ester solvents. For certain trimming compositions, an alcohol and/or ester solvent may provide enhanced solubility with respect to the solid components. Suitable alcohol solvents include, for example: straight, branched or cyclic C4-C8 monohydric alcohol such as 1-butanol, 2-butanol, isobutyl alcohol, tert-butyl alcohol, 3-methyl-1-butanol, 1-pentanol, 2-pentanol, 4-methyl-2-pentanol, 1-hexanol, 1-heptanol, 2-hexanol, 2-heptanol, 3-hexanol, 3-heptanol, 1-octanol, 2-octanol, 3-octanol, 4-octanol, 2,2,3,3,4,4-hexafluoro-1-butanol, 2,2,3,3,4,4,5,5-octafluoro-1-pentanol and 2,2,3,3,4,4,5,5,6,6-decafluoro-1-hexanol; and C5-C9 fluorinated diols such as 2,2,3,3,4,4-hexafluoro-1,5-pentanediol, 2,2,3,3,4,4,5,5-octafluoro-1,6-hexanediol and 2,2,3,3,4,4,5,5,6,6,7,7-dodecafluoro-1,8-octanediol. The alcohol solvent is preferably a C4-C8 monohydric alcohol, with 4-methyl-2-pentanol being preferred. Suitable ester solvents include, for example, alkyl esters having a total carbon number of from 4 to 10 such as alkyl propionates such as n-butyl propionate, n-pentyl propionate, n-hexyl propionate and n-heptyl propionate, and alkyl butyrates such as n-butyl butyrate, isobutyl butyrate and isobutyl isobutyrate. The one or more alcohol and/or ester solvents if used in the ether-containing solvent system are present in a combined amount of from 2 to 50 wt %, more typically in an amount of from 2 to 30 wt %, based on the solvent system.

The ether-containing solvent system can include one or more additional solvents chosen, for example, from one or more of: ketones such as 2,5-dimethyl-4-hexanone and 2,6-dimethyl-4-heptanone; aliphatic hydrocarbons such as n-heptane, 2-methylheptane, 3-methylheptane, 3,3-dimethylhexane, 2,3,4-trimethylpentane, n-octane, n-nonane, and n-decane; fluorinated aliphatic hydrocarbons such as perfluoroheptane; and diethers such as dipropylene glycol monomethyl ether. Such additional solvents, if used, are typically present in a combined amount of from 1 to 20 wt % based on the solvent system.

A particularly preferred organic-based solvent system includes one or more monoether solvents in a combined amount of from 70 to 98 wt % based on the solvent system, and one or more alcohol and/or ester solvents in a combined amount of from 2 to 30 wt % based on the solvent system. The one or more solvents making up the organic-based solvent system are typically present in the overcoat composition in a combined amount of from 90 to 99 wt %, preferably from 95 to 99 wt %, based on the overcoat composition.

The trimming composition can further include one or more additional, optional component, for example, a surfactant. Typical surfactants include those which exhibit an amphiphilic nature, meaning that they can be both hydrophilic and hydrophobic at the same time. Amphiphilic surfactants possess a hydrophilic head group or groups, which have a strong affinity for water and a long hydrophobic tail, which is organophilic and repels water. Suitable surfactants can be ionic (i.e., anionic, cationic) or nonionic. Further examples of surfactants include silicone surfactants, poly (alkylene oxide) surfactants, and fluorochemical surfactants. Suitable non-ionic surfactants include, but are not limited to, octyl and nonyl phenol ethoxylates such as TRITON® X-114, X-100, X-45, X-15 and branched secondary alcohol ethoxylates such as TERGITOL™ TMN-6 (The Dow Chemical Company, Midland, Mich. USA). Still further exemplary surfactants include alcohol (primary and secondary) ethoxylates, amine ethoxylates, glucosides, glucamine, polyethylene glycols, poly(ethylene glycol-co-propylene glycol), or other surfactants disclosed in *McCutcheon's Emulsifers and Detergents*, North American Edition for the Year 2000 published by Manufacturers Confectioners Publishing Co. of Glen Rock, N.J. Nonionic surfactants that are acetylenic diol derivatives also can be suitable. Such surfactants are commercially available from Air Products and Chemicals, Inc. of Allentown, Pa. and sold under the trade names of SURFYNOL® and DYNOL®. Additional suitable surfactants include other polymeric compounds such as the tri-block EO-PO-EO co-polymers PLURONIC® 25R2, L121, L123, L31, L81, L101 and P123 (BASF, Inc.). Such surfactant and other optional additives if used are typically present in the composition in minor amounts such as from 0.01 to 10 wt % based on total solids of the trimming composition. The trimming compositions are preferably free of cross-linking agents as such materials can result in a dimensional increase of the photoresist pattern. The trimming compositions can be free of polymeric acids and polymeric acid generators.

The trimming compositions can be prepared following known procedures. For example, the compositions can be prepared by dissolving solid components of the composition in the solvent components. The desired total solids content of the compositions will depend on factors such as the desired final layer thickness. Preferably, the solids content of the trimming compositions is from 1 to 10 wt %, more preferably from 1 to 5 wt %, based on the total weight of the composition.

Pattern Formation Methods

Processes in accordance with the invention will now be described with reference to FIG. 1A-H, which illustrates an exemplary process flow for a pattern formation method in accordance with the invention. While the illustrated process flow describes a patterning process in which a single resist mask is used to transfer the photoresist pattern to the underlying substrate, it should be clear that the method can be used in other lithographic processes, for example, in double patterning processes such as litho-litho-etch (LLE), litho-etch-litho-etch (LELE) or self-aligned double patterning (SADP), as an ion implantation mask, or any other lithographic process where such photoresist pattern treatment would be beneficial.

FIG. 1A depicts in cross-section a substrate 100 which may include various layers and features. The substrate can be of a material such as a semiconductor, such as silicon or a compound semiconductor (e.g., III-V or II-VI), glass, quartz, ceramic, copper and the like. Typically, the substrate is a semiconductor wafer, such as single crystal silicon or compound semiconductor wafer, and may have one or more layers and patterned features formed on a surface thereof. One or more layers to be patterned 102 may be provided over the substrate 100. Optionally, the underlying base substrate material itself may be patterned, for example, when it is desired to form trenches in the substrate material. In the case of patterning the base substrate material itself, the pattern shall be considered to be formed in a layer of the substrate.

The layers may include, for example, one or more conductive layers such as layers of aluminum, copper, molybdenum, tantalum, titanium, tungsten, alloys, nitrides or silicides of such metals, doped amorphous silicon or doped polysilicon, one or more dielectric layers such as layers of silicon oxide, silicon nitride, silicon oxynitride, or metal oxides, semiconductor layers, such as single-crystal silicon, and combinations thereof. The layers to be etched can be formed by various techniques, for example, chemical vapor deposition (CVD) such as plasma-enhanced CVD (PECVD), low-pressure CVD (LPCVD) or epitaxial growth, physical vapor deposition (PVD) such as sputtering or evaporation, or electroplating. The particular thickness of the one or more layers to be etched 102 will vary depending on the materials and particular devices being formed.

Depending on the particular layers to be etched, film thicknesses and photolithographic materials and process to be used, it may be desired to dispose over the layers 102 a hard mask layer 103 and/or a bottom antireflective coating (BARC) 104 over which a photoresist layer 106 is to be coated. Use of a hard mask layer may be desired, for example, with very thin resist layers, where the layers to be etched require a significant etching depth, and/or where the particular etchant has poor resist selectivity. Where a hard mask layer is used, the resist patterns to be formed can be transferred to the hard mask layer 103 which, in turn, can be used as a mask for etching the underlying layers 102. Suitable hard mask materials and formation methods are known in the art. Typical materials include, for example, tungsten, titanium, titanium nitride, titanium oxide, zirconium oxide, aluminum oxide, aluminum oxynitride, hafnium oxide, amorphous carbon, spin-on-carbon (SOC), silicon oxynitride and silicon nitride. The hard mask layer can include a single layer or a plurality of layers of different materials. The hard mask layer can be formed, for example, by CVD, PVD, or spin-coating techniques.

A bottom antireflective coating may be desirable where the substrate and/or underlying layers would otherwise reflect a significant amount of incident radiation during photoresist exposure such that the quality of the formed pattern would be adversely affected. Such coatings can improve depth-of-focus, exposure latitude, linewidth uniformity and CD control. Antireflective coatings are typically used where the resist is exposed to deep ultraviolet radiation (300 nm or less), for example, KrF (248 nm), ArF (193 nm) or EUV (13.5 nm) radiation. The antireflective coating can comprise a single layer or a plurality of different layers. Suitable antireflective materials and methods of formation are known in the art. Antireflective materials are commercially available, for example, those sold under the AR™ tradename by the Specialty Products Division of DowDupont (Wilmington, Del. USA), such as AR™ 3, AR™ 40A and AR™ 124 antireflectant materials.

A photoresist layer 106 is formed from a photoresist composition, typically a chemically amplified photosensitive composition comprising a polymer having acid labile groups, a photoacid generator and a solvent. Suitable photoresist compositions are well known in the art. Preferably, the photoresist polymers are formed from monomers chosen from vinyl aromatic (e.g., styrene and hydroxystyrene), (meth)acrylate, norbornene, and combinations thereof. In a preferred aspect, the photoresist polymer is vinyl aromatic-based, wherein more than 50 mol % of the polymerized units in the polymer, typically more than 80 mol % of the polymerized units in the polymer, are formed from vinyl aromatic monomers.

The photoresist layer is disposed on the substrate over the antireflective layer 104 (if present). The photoresist composition can be applied to the substrate by spin-coating, dipping, roller-coating or other conventional coating technique. Of these, spin-coating is typical. For spin-coating, the solids content of the coating solution can be adjusted to provide a desired film thickness based upon the specific coating equipment utilized, the viscosity of the solution, the speed of the coating tool and the amount of time allowed for spinning. A typical thickness for the photoresist layer 106 is from about 500 to 3000 Å.

The photoresist layer 106 is typically next softbaked to minimize the solvent content in the layer, thereby forming a tack-free coating and improving adhesion of the layer to the substrate. The softbake can be conducted on a hotplate or in an oven, with a hotplate being typical. The softbake temperature and time will depend, for example, on the particular material of the photoresist and thickness. Typical softbakes are conducted at a temperature of from about 90 to 150° C., and a time of from about 30 to 90 seconds.

The photoresist layer 106 is next exposed to activating radiation 108 through a photomask 110 to create a difference in solubility between exposed and unexposed regions. References herein to exposing a photoresist composition to radiation that is activating for the composition indicates that the radiation is capable of forming a latent image in the photoresist composition. The photomask has optically transparent and optically opaque regions corresponding to regions of the resist layer to be exposed and unexposed, respectively, by the activating radiation. The exposure wavelength is typically sub-400 nm, sub-300 nm, such as deep-UV (248 nm), 193 nm or an EUV wavelength (e.g., 13.5 nm). In a preferred aspect, the exposure wavelength is deep-UV or EUV lithography. The exposure energy is typically from about 10 to 80 mJ/cm$^2$, depending, for example, on the exposure tool and the components of the photosensitive composition.

Following exposure of the photoresist layer 106, a post-exposure bake (PEB) is typically performed. The PEB can be conducted, for example, on a hotplate or in an oven. Conditions for the PEB will depend, for example, on the particular photoresist composition and layer thickness. The PEB is typically conducted at a temperature of from about 80 to 150° C., and a time of from about 30 to 90 seconds. A latent image defined by the boundary between polarity-switched and unswitched regions (corresponding to exposed and unexposed regions, respectively) is thereby formed.

Figure 1E:
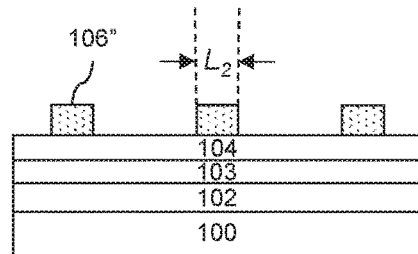
Figure 1B:
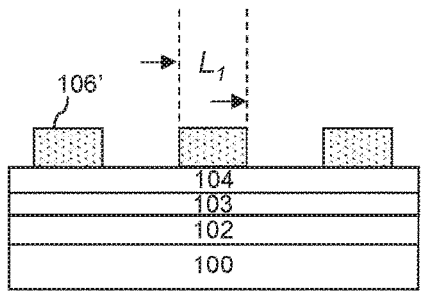

The photoresist layer 106 is next developed to remove exposed regions of the layer, leaving unexposed regions forming a resist pattern 106' having a plurality of features as shown in FIG. 1B. The features are not limited and can include, for example, a plurality of lines, pillars and/or contact hole patterns which allow for the formation of such patterns in the underlying layers to be patterned. The formed resist patterns have an initial dimension shown as $L_1$, a linewidth for line patterns, post diameter for post patterns, or sidewall width for contact hole patterns.

Figure 1F:
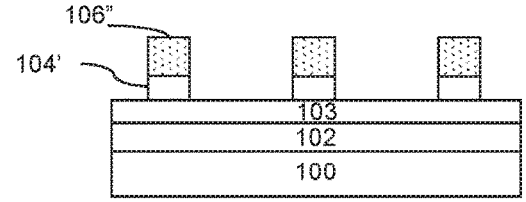
Figure 1C:
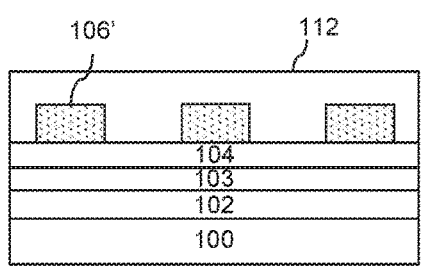

A layer 112 of a photoresist pattern trimming composition as described herein is formed over the photoresist pattern 106' as shown in FIG. 1C. The trimming composition is typically applied to the substrate by spin-coating. The solids content of the coating solution can be adjusted to provide a desired film thickness based upon the specific coating equipment utilized, the viscosity of the solution, the speed of the coating tool and the amount of time allowed for spinning. A typical thickness for the pattern trimming composition layer 112 is from 200 to 1500 Å, typically measured on an unpatterned substrate.

Figure 1G:
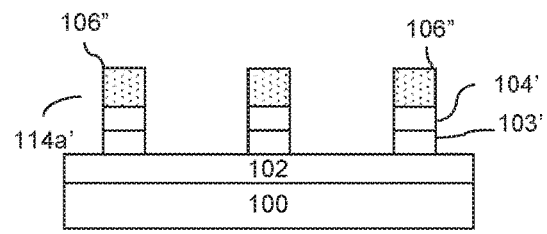
Figure 1D:
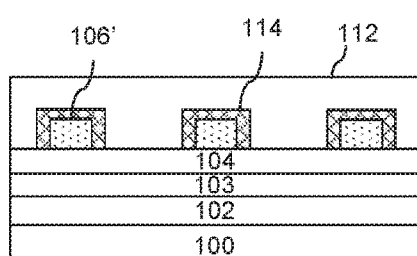

As shown in FIG. 1D, the substrate is next baked to remove solvent in the trimming composition layer. The bake also allows the acid of the trimming composition to diffuse into the surface of the resist pattern 106' to cause a polarity-changing reaction in the resist pattern surface region 114. The bake can be conducted with a hotplate or oven, with a hotplate being typical. Suitable bake temperatures are greater than 50° C., for example, greater than 70° C., greater than 90° C., greater than 120° C. or greater than 150° C., with a temperature of from 70 to 160° C. and a time of from about 30 to 90 seconds being typical. While a single baking step is typical, multiple-step baking can be used and may be useful for resist profile adjustment.

The photoresist pattern is next contacted with a rinsing agent, typically a developing solution, to remove the residual trimming composition layer 112 and typically also the surface region 114 of the photoresist pattern, with the resulting pattern 106" being shown in FIG. 1E. The rinsing agent is typically an aqueous alkaline developer, for example, an aqueous quaternary ammonium hydroxide solution, for example, a tetra-alkyl ammonium hydroxide solution such as a tetramethylammonium hydroxide (TMAH) solution, typically 0.26 Normality (N) (2.38 wt %) TMAH. The rinsing agent can in a further aspect be water. The resulting structure is shown in FIG. 1E. The resist pattern after trimming treatment has a dimension ($L_2$) that is smaller as compared with the feature size prior to trimming treatment.

Figure 1H:
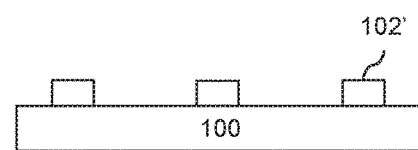

Using the resist pattern 106" as an etch mask, the BARC layer 104 is selectively etched to form BARC patterns 104', exposing the underlying hardmask layer 103, as shown in FIG. 1F. The hardmask layer is next selectively etched, again using the resist pattern as an etch mask, resulting in patterned BARC and hardmask layer 103', as shown in FIG. 1G. Suitable etching techniques and chemistries for etching the BARC layer and hardmask layer are known in the art and will depend, for example, on the particular materials of these layers. Dry-etching processes such as reactive ion etching are typical. The resist pattern 106" and patterned BARC layer 104' are next removed from the substrate using known techniques, for example, oxygen plasma ashing. Using the hardmask pattern 103' as an etch mask, the one or more layers 102 are then selectively etched. Suitable etching techniques and chemistries for etching the underlying layers 102 are known in the art, with dry-etching processes such as reactive ion etching being typical. The patterned hardmask layer 103' can next be removed from the substrate surface using known techniques, for example, a dry-etching process such as reactive ion etching or a wet strip. The resulting structure is a pattern of etched features 102' as illustrated in FIG. 1H. In an alternative exemplary method, it may be desirable to pattern the layer 102 directly using the photoresist pattern 106" without the use of a hardmask layer 103. Whether direct patterning with the resist patterns can be employed will depend on factors such as the materials involved, resist selectivity, resist pattern thickness and pattern dimensions.

The following non-limiting examples are illustrative of the invention.

EXAMPLES

Polymer Synthesis

The following monomers were used to synthesize polymers according to the procedures described below:

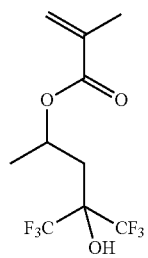

M1

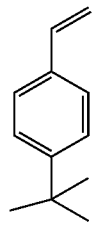

M2

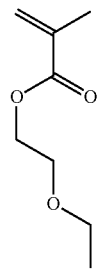

M3

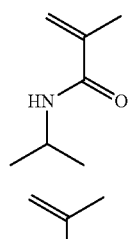

M4

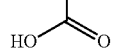

M5

Polymer P1 Synthesis Example 1

A monomer feed solution was prepared by mixing 8.78 g Methyl isobutyl carbinol (MIBC) and 40.50 g Monomer M1 in a first container. An initiator feed solution was prepared by combining 1.91 g Vazo-67 free radical initiator (E. I. du Pont de Nemours and Company) and 17.20 g MIBC in a second container and agitating the mixture to dissolve the initiator. 22.00 g MIBC was introduced into a reaction vessel and the vessel was purged with nitrogen gas for 30 minutes. The reaction vessel was next heated to 90° C. with agitation. Introduction of the monomer feed solution and initiator feed solution into the reaction vessel was simultaneously started. The monomer feed solution was fed over a period of two hours and the initiator feed solution was fed over a period of three hours. The reaction vessel was maintained at 90° C. for an additional seven hours with agitation, and was then allowed to cool to room temperature. The reaction mixture was precipitated from heptane (20×) to yield Polymer P1 as white solids (32 g, 80% yield). Weight average molecular weight (Mw) and number average molecular weight (Mn) were determined by polystyrene equivalent value as measured by gel permeation chromatography (GPC), and polydispersity was calculated as PDI=Mw/Mn. The monomer ratios in the polymer and molecular weight results are shown in Table 1.

Polymer P2 Synthesis Example 2

A monomer feed solution was prepared by dissolving 10.46 g Monomer M2, 5.16 g Monomer M3 and 5.63 g Monomer M5 in 190 g ethyl lactate in a reaction vessel, and the solution was heated to 165° C. An initiator feed solution was prepared by combining 3.40 g V-601 free radical initiator (Wako Chemical Company) and 34.50 g ethyl lactate in a container and agitating the mixture to dissolve the initiator. The initiator feed solution was fed to the reaction vessel over a period of 0.5 hours. The reaction vessel was maintained at 165° C. for an additional 24 hours with agitation, and was then allowed to cool to room temperature. The reaction mixture was precipitated from methanol:water 75:25 (wt %) (20×) to yield Polymer P2 as white solids (17 g, 81% yield). Mw, Mn and PDI were determined as described in Example 1. The monomer ratios in the polymer and molecular weight results are shown in Table 1.

Polymer P3 Synthesis Example 3

A monomer feed solution was prepared by dissolving 11.98 g Monomer M2, 1.90 g Monomer M4 and 5.13 g Monomer M5 in 108 g ethyl lactate, and the solution was heated to 165° C. An initiator feed solution was prepared by combining 1.52 g V-601 free radical initiator (Wako Chemical Company) and 70.00 g ethyl lactate in a container and agitating the mixture to dissolve the initiator. The initiator feed solution was fed to the reaction vessel over a period of 0.5 hours. The reaction vessel was maintained at 165° C. for an additional 24 hours with agitation, and was then allowed to cool to room temperature. The reaction mixture was precipitated from methanol:water 75/25 (wt %) (20×) to yield Polymer P3 as white solids (15 g, 79% yield). Mw, Mn and PDI were determined as described in Example 1. The monomer ratios in the polymer and molecular weight results are shown in Table 1.

Polymer P4 Synthesis Example 4

A monomer feed solution was prepared by dissolving 11 g Monomer M2, 2.72 g Monomer M3 and 7.44 g Monomer M5 in 190 g ethyl lactate in a reaction vessel, and the solution was heated to 165° C. An initiator feed solution was prepared by combining 3.40 g V-601 free radical initiator (Wako Chemical Company) and 34.40 g ethyl lactate in a container and agitating the mixture to dissolve the initiator. The initiator feed solution was fed to the reaction vessel over a period of 0.5 hour. The reaction vessel was maintained at 165° C. for an additional 24 hours with agitation, and was then allowed to cool to room temperature. The reaction mixture was precipitated from methanol:water 75/25 (wt %) (20×) to yield Polymer P4 as white solids (18 g, 86%). The monomer ratios in the polymer and molecular weight results are shown in Table 1.

Polymer P5 Synthesis Example 5

A monomer feed solution was prepared by dissolving 12.93 g Monomer M2, 4.80 g Monomer M3 and 7.80 g Monomer M5 in 230 g ethyl lactate in a reaction vessel, and the solution was heated to 165° C. An initiator feed solution was prepared by combining 4.00 g V-601 free radical initiator (Wako Chemical Company) and 41.00 g of ethyl lactate in a container and agitating the mixture to dissolve the initiator. The initiator feed solution was fed to the reaction vessel over a period of 0.5 hours. The reaction vessel was maintained at 165° C. for an additional 24 hours with agitation, and was then allowed to cool to room temperature. The reaction mixture was precipitated from methanol:water 75/25 (wt %) (20×) to yield Polymer P5 as white solids (17.5 g, 82% yield). The monomer ratios in the polymer and molecular weight results are shown in Table 1.

TABLE 1

| Example | Polymer | M1 (mol %) | M2 (mol %) | M3 (mol %) | M4 (mol %) | M5 (mol %) | Mw (Da) | Mn (Da) | PDI |
|---|---|---|---|---|---|---|---|---|---|
| Ex. 1 | P1 | 100 | | | | | 15966 | 8268 | 1.93 |
| Ex. 2 | P2 | | 40 | 20 | | 40 | 4305 | 1926 | 2.24 |
| Ex. 3 | P3 | | 50 | | 10 | 40 | 6034 | 2591 | 2.33 |
| Ex. 4 | P4 | | 40 | 10 | | 50 | 4268 | 1936 | 2.2 |
| Ex. 5 | P5 | | 40 | 15 | | 45 | 3396 | 1682 | 2.02 |

Acid Synthesis

The following acids were used in pattern trimming compositions as described below. Acids A1-A3 were synthesized according to the following procedures and the remaining acids were commercially obtained.

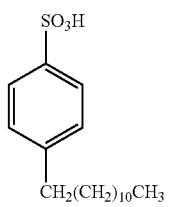

A1

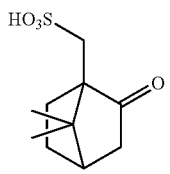

A2

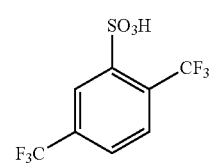

A3

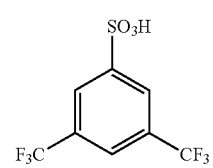

A4

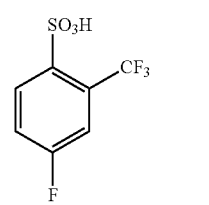

A5

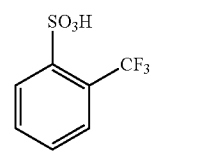

A6

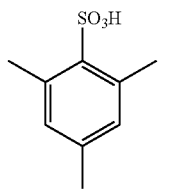

A7

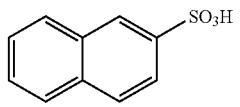

A8

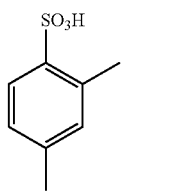

A9

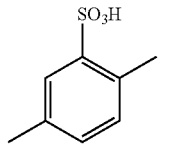

A10

-continued

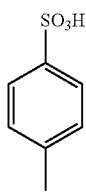

A11

Acid A1 Synthesis Example 6

25 g 2,5-bis(trifluoromethyl)benzenesulfonyl chloride was dissolved in 15 g water and refluxed for 24 hours. Upon cooling, the reaction mixture was evaporated and dried under vacuum to yield white solids of acid A1 (20 g, 90% yield). [$^1$H NMR ((CD$_3$)$_2$CO, 600 MHz): δ 8.04 (m, 1H), 8.08 (m, 1H), 8.50 (s, 1H), 9.52 (bs, 1H). $^{13}$C NMR ((CD$_3$)$_2$CO, 600 MHz): δ 122.37, 123.71, 127.57, 127.59, 128.75, 130.48, 133.27, 144.70. $^{19}$F NMR ((CD$_3$)$_2$CO, 600 MHz): δ −63.93, −58.80].

Acid A2 Synthesis Example 7

Acid A2 was synthesized according to a procedure similar to that described for Acid A1. White solids of Acid A2 resulted (19 g, 85.5% yield). [$^1$H NMR ((CD$_3$)$_2$CO, 600 MHz): δ 8.15 (s, 1H), 8.34 (s, 2H), 10.81 (bs, 1H). $^{13}$C NMR ((CD$_3$)$_2$CO, 600 MHz): δ 123.94, 124.22, 126.56, 131.51, 146.79. $^{19}$F NMR ((CD$_3$)$_2$CO, 600 MHz): δ −63.51].

Acid A3 Synthesis Example 8

Acid A3 was synthesized according to a procedure similar to that described for Acid A1. White solids of Acid A3 resulted (18 g, 81% yield). [$^1$H NMR ((CD$_3$)$_2$CO, 600 MHz): δ 7.61 (m, 1H), 7.71 (m, 1H), 8.33 (m, 1H), 10.83 (bs, 1H). $^{13}$C NMR ((CD$_3$)$_2$CO, 600 MHz): δ 115.58, 115.71, 123.20, 131.20, 133.72, 136.86, 162.79, 164.46. $^{19}$F NMR ((CD$_3$)$_2$CO, 600 MHz): δ −98.75, −58.20].

Preparation of Pattern Trimming Compositions

Photoresist pattern trimming compositions (PTCs) were prepared by dissolving solid components in solvents using the materials and amounts set forth in Table 2. The resulting mixtures, made on a 14-30 g scale, were shaken on a mechanical shaker for from 3 to 24 hours and then filtered through a PTFE disk-shaped filter having a 0.2 micron pore size.

TABLE 2

| Example | Pattern Trimming Composition | Polymer (wt %) | Acid (wt %) | Solvent (wt %) | | |
|---|---|---|---|---|---|---|
| | | | | S1 | S2 | S3 |
| Ex. 9 | PTC-1 | P1 (2.970) | A1 (0.030) | 87.30 | 9.70 | |
| Ex. 10 | PTC-2 | P1 (2.910) | A1 (0.090) | 87.30 | 9.70 | |
| Ex. 11 | PTC-3 | P1 (2.985) | A2 (0.015) | 87.30 | 9.70 | |
| Ex. 12 | PTC-4 | P1 (2.940) | A2 (0.060) | 82.45 | 14.55 | |
| Ex. 13 | PTC-5 | P1 (2.970) | A2 (0.030) | 87.30 | 9.70 | |
| Ex. 14 | PTC-6 | P1 (2.910) | A2 (0.090) | 82.45 | 14.55 | |
| Ex. 15 | PTC-7 | P1 (2.910) | A2 (0.090) | 87.30 | 9.70 | |
| Ex. 16 | PTC-8 | P1 (2.970) | A3 (0.090) | 87.30 | 9.70 | |
| Ex. 17 | PTC-9 | P1 (2.910) | A3 (0.090) | 87.30 | 9.70 | |
| Ex. 18 | PTC-10 | P1 (2.910) | A3 (0.090) | 27.16 | 1.94 | 67.90 |
| Ex. 19 | PTC-11 | P2 (2.910) | A3 (0.090) | 87.30 | 9.70 | |
| Ex. 20 | PTC-12 | P2 (2.910) | A3 (0.090) | 27.16 | 1.94 | 67.90 |
| Ex. 21 | PTC-13 | P2 (2.910) | A2 (0.090) | 97.00 | | |
| Ex. 22 | PTC-14 | P2 (2.850) | A2 (0.150) | 87.30 | 9.70 | |
| Ex. 23 | PTC-15 | P3 (2.910) | A2 (0.090) | 97.00 | | |
| Ex. 24 | PTC-16 | P4 (2.910) | A2 (0.090) | 87.30 | 9.70 | |
| Ex. 25 | PTC-17 | P4 (2.850) | A2 (0.150) | 87.30 | 9.70 | |
| Ex. 26 | PTC-18 | P5 (2.910) | A2 (0.090) | 87.30 | 9.70 | |
| Ex. 27 (Comp.) | PTC-19 | P1 (2.970) | A4 (0.030) | 87.30 | 9.70 | |
| Ex. 28 (Comp.) | PTC-20 | P1 (2.910) | A4 (0.090) | 87.30 | 9.70 | |
| Ex. 29 (Comp.) | PTC-21 | P1 (2.880) | A4 (0.120) | 87.30 | 9.70 | |
| Ex. 30 (Comp.) | PTC-22 | P1 (2.910) | A5 (0.090) | 82.45 | 14.55 | |
| Ex. 31 (Comp.) | PTC-23 | P1 (2.760) | A5 (0.240) | 82.45 | 14.55 | |
| Ex. 32 (Comp.) | PTC-24 | P1 (2.820) | A6 (0.180) | 87.30 | 9.70 | |
| Ex. 33 (Comp.) | PTC-25 | P1 (2.940) | A7 (0.060) | 87.30 | 9.70 | |
| Ex. 34 (Comp.) | PTC-26 | P1 (3.165) | A8 (0.275) | 86.904 | 9.656 | |
| Ex. 35 (Comp.) | PTC-27 | P1 (3.371) | A9 (0.069) | 86.904 | 9.656 | |
| Ex. 36 (Comp.) | PTC-28 | P1 (3.371) | A10 (0.069) | 86.904 | 9.656 | |
| Ex. 37 (Comp.) | PTC-29 | P1 (3.337) | A11 (0.103) | 86.904 | 9.656 | |

S1 = Isoamyl ether; S2 = Methyl isobutyl carbinol (MIBC); S3 = Isobutyl isobutyrate; All amounts provided as weight percent (wt %) based on total pattern trimming composition.

Photoresist Pattern Trimming Composition Evaluation
Critical Dimension (CD) and Linewidth Roughness (LWR) Evaluation 200 mm silicon wafers were coated with AR™ 3 organic bottom antireflective coating (BARC) material (Dow Electronic Materials) and cured at 205° C. for 60 seconds to a thickness of 600 Å on a TEL Clean Track Act 8 coating tool. UV™ 217G-0.25 polyhydroxystyrene-based positive-tone photoresist (Dow Electronic Materials) was coated over the BARC layer and the wafers were softbaked at 130° C. for 60 seconds to a target thickness of 3550 Å on a TEL Clean Track Act 8 coating tool. The coated wafers were exposed to KrF (248 nm) radiation on a Canon FPA-5000 ES4 DUV scanner with NA=0.68, conventional illumination (Sigma, 0.75) using a binary reticle with 140 nm dense trench (1:1 line-space) patterns. The wafers were post-exposure baked at 125° C. for 60 seconds, developed with 0.26 N aqueous TMAH solution for 45 seconds, rinsed with distilled water and spun dry on a TEL Clean Track Act 8 coating tool. Resist pattern CD and LWR measurements were made using a Hitachi High Technologies Co. CG4000 CD-SEM to obtain initial CD and LWR values. The wafers were next coated with 400 Å of a respective pattern trimming composition, baked for 60 seconds at a temperature described in Table 3, rinsed with 0.26 N aqueous TMAH solution for 30 seconds, rinsed with distilled water and spun dry on a TEL Clean Track Act 8 coating tool. CD and LWR measurements of the resist patterns for the treated wafers were then made to obtain final CD and LWR values. The change in CD ($\Delta$CD) for the treated patterns was calculated according to the following equation:

$$\Delta CD = CD_f - CD_i$$

wherein $CD_f$ is the average CD measurement after pattern trimming treatment, and $CD_i$ is the average CD measurement prior to pattern trimming treatment. The results are shown in Table 3.

Pattern Collapse Margin (PCM) Evaluation 200 mm silicon wafers were coated with AR™ 3 organic bottom antireflectiv coating (BARC) material (DuPont) and cured at 205° C. for 60 seconds to a thickness of 600 Å on a TEL Clean Track Act 8 coating tool. UV™ 217G-0.25 polyhydroxystyrene-based positive-tone photoresist (DuPont) was coated over the BARC layer and the wafers were softbaked at 130° C. for 60 seconds to a target thickness of 3550 Å on a TEL Clean Track Act 8 coating tool. The coated wafers were exposed to KrF (248 nm) radiation at various doses from 466 J/m² to 626 J/m² on a Canon FPA-5000 ES4 DUV scanner with NA=0.68, conventional illumination (Sigma, 0.75) using a binary reticle with 140 nm dense trench (1:1 line-space) patterns. The wafers were post-exposure baked at 125° C. for 60 seconds, developed with 0.26 N aqueous TMAH solution for 45 seconds, rinsed with distilled water and spun dry on a TEL Clean Track Act 8 coating tool. The wafers were next coated with 400 Å of a respective pattern trimming composition, baked for 60 seconds at a temperature described in Table 3, and rinsed with 0.26 N aqueous TMAH solution for 30 seconds, rinsed with distilled water and spun dry on a TEL Clean Track Act 8 coater/developer. CDs of the resist patterns for the treated wafers were then measured as described above. The SEM images of the patterns were observed for the occurrence of pattern collapse. The CDs of the largest non-collapsed trenches (PCM) are reported in Table 3, with a larger PCM value indicating better pattern collapse margin performance.

TABLE 3

| Example | Pattern Trimming Composition | Bake Temp. (° C.) | ΔCD (nm) | PCM (nm) | LWR (nm) |
| --- | --- | --- | --- | --- | --- |
| Ex. 38 | PTC-1 | 90 | 22.7 | 179 | 8.7 |
| Ex. 39 | PTC-1 | 110 | 24.9 | 176 | 8.8 |
| Ex. 40 | PTC-2 | 90 | 27.1 | 177 | 8.6 |
| Ex. 41 | PTC-2 | 110 | 36.4 | 176 | 8.5 |
| Ex. 42 | PTC-3 | 80 | 23.3 | 180 | 9.1 |
| Ex. 43 | PTC-3 | 90 | 22.6 | 177 | 8.9 |
| Ex. 44 | PTC-3 | 100 | 22.2 | 178 | 8.8 |
| Ex. 45 | PTC-4 | 80 | 30.3 | 181 | 8.6 |
| Ex. 46 | PTC-4 | 90 | 40.6 | 184 | 8.3 |
| Ex. 47 | PTC-4 | 100 | 45.0 | 183 | 8.4 |
| Ex. 48 | PTC-5 | 90 | 27.8 | 177 | 8.8 |
| Ex. 49 | PTC-5 | 110 | 29.5 | 178 | 8.5 |
| Ex. 50 | PTC-6 | 80 | 30.2 | 181 | 8.6 |
| Ex. 51 | PTC-6 | 90 | 40.1 | 184 | 8.3 |
| Ex. 52 | PTC-6 | 100 | 45 | 183 | 8.4 |
| Ex. 53 | PTC-6 | 110 | 53.2 | 186 | 8.5 |
| Ex. 54 | PTC-7 | 90 | 31.3 | 175 | 8.6 |
| Ex. 55 | PTC-7 | 110 | 43.5 | 180 | 8.4 |
| Ex. 56 | PTC-8 | 80 | 24.8 | 180 | 8.5 |
| Ex. 57 | PTC-8 | 100 | 27.5 | 180 | 8.8 |
| Ex. 58 | PTC-9 | 80 | 29.3 | 180 | 9.0 |
| Ex. 59 | PTC-9 | 90 | 33.7 | 178.8 | 8.8 |
| Ex. 60 | PTC-9 | 100 | 38.8 | 181 | 8.8 |
| Ex. 61 | PTC-10 | 90 | 45.1 | 189.1 | 9.2 |
| Ex. 62 | PTC-11 | 90 | 40.7 | 191.3 | 9.4 |
| Ex. 63 | PTC-12 | 90 | 53.1 | 188.9 | 9.3 |
| Ex. 64 | PTC-13 | 90 | 33.6 | 188.5 | 9.3 |
| Ex. 65 | PTC-13 | 110 | 35.5 | 185.3 | 8.9 |
| Ex. 66 | PTC-14 | 90 | 36.7 | 189.2 | 9.1 |
| Ex. 67 | PTC-15 | 90 | 29.2 | 189 | 9.0 |
| Ex. 68 | PTC-16 | 90 | 32.1 | 183.2 | 9.1 |
| Ex. 69 | PTC-17 | 80 | 34.7 | * | 8.7 |
| Ex. 70 | PTC-17 | 90 | 36.4 | 182.8 | 8.6 |
| Ex. 71 | PTC-17 | 100 | 41.6 | * | 9.0 |
| Ex. 72 | PTC-18 | 90 | 33.9 | * | 8.8 |
| Ex. 73 | PTC-19 | 110 | 28.9 | 173.1 | 9.5 |
| Ex. 74 | PTC-20 | 110 | 45.5 | 175.7 | 9.2 |
| Ex. 75 | PTC-22 | 80 | 37.1 | 183.1 | 10.4 |
| Ex. 76 | PTC-22 | 90 | 36.5 | 183.8 | 10.3 |
| Ex. 77 (Comp.) | PTC-22 | 100 | 34.5 | 183.9 | 10.6 |
| Ex. 78 (Comp.) | PTC-22 | 110 | 35.3 | 182.9 | 10.5 |
| Ex. 79 (Comp.) | PTC-23 | 80 | 29 | 183.2 | 9.2 |
| Ex. 80 (Comp.) | None | — | 0 | 170 | 10.0 |

* PCM not evaluated.

Coating Defect Evaluation

Pattern trimming compositions were spin-coated at 1500 rpm on respective 200 mm Si wafers. The coated wafers were baked at 80° C. for 60 seconds. The wafers were then inspected on a KLA-Tencor 2800/Surfscan SP2 wafer surface inspection system. The system measured defects having a size greater than 45 nm. Two wafers were run consecutively for each pattern trimming composition tested, with the lower of the two measured defect values for each composition tested being provided in Table 4.

TABLE 4

| Example | Pattern Trimming Composition | Total Defects |
| --- | --- | --- |
| Ex. 81 | PTC-2 | 29 |
| Ex. 82 | PTC-3 | 23 |
| Ex. 83 | PTC-11 | 11 |
| Ex. 84 | PTC-14 | 91 |
| Ex. 85 (Comp.) | PTC-21 | >50K* |
| Ex. 86 (Comp.) | PTC-23 | 813 |
| Ex. 87 (Comp.) | PTC-24 | >50K* |
| Ex. 88 (Comp.) | PTC-25 | 650 |
| Ex. 89 (Comp.) | PTC-26 | >50K* |
| Ex. 90 (Comp.) | PTC-27 | 1394 |

TABLE 4-continued

| Example | Pattern Trimming Composition | Total Defects |
|---|---|---|
| Ex. 91 (Comp.) | PTC-28 | 1250 |
| Ex. 92 (Comp.) | PTC-29 | >50K* |

*>50K total defects is the upper limit detected.

What is claimed is:

1. A photoresist pattern trimming composition, comprising a polymer, an aromatic sulfonic acid, and an organic-based solvent system, wherein the aromatic sulfonic acid is of general formula (I):

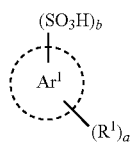

(I)

wherein: $Ar^1$ represents a substituted or unsubstituted aromatic group; $R^1$ independently represents a fluorine atom or trifluoromethyl, and wherein an $R^1$ represents trifluoromethyl; a represents an integer of 2 or more; and b represents an integer of 1 or more, provided that a+b is at least 3 and is not greater than the total number of available aromatic carbon atoms of $Ar^1$.

2. The photoresist pattern trimming composition of claim 1, wherein the aromatic sulfonic acid is of general formula II:

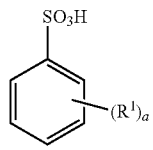

(II)

wherein: $R^1$ independently represents a fluorine atom or trifluoromethyl, and wherein an $R^1$ represents trifluoromethyl and a represents an integer of from 2 to 5.

3. The photoresist pattern trimming composition of claim 1, wherein the polymer comprises a repeat unit formed from a vinyl aromatic monomer.

4. The photoresist pattern trimming composition of claim 1, wherein the organic-based solvent comprises a monoether.

5. The photoresist pattern trimming composition of claim 4, wherein the organic-based solvent further comprises an alcohol and/or an ester.

6. The photoresist pattern trimming composition of claim 1, wherein the composition is free of polymeric acids and polymeric acid generators.

7. The photoresist pattern trimming composition of claim 1, wherein a first $R^1$ represents trifluoromethyl and a second $R^1$ represents a fluorine atom.

8. A pattern formation method, comprising:
(a) providing a semiconductor substrate;
(b) forming a photoresist pattern over the semiconductor substrate, wherein the photoresist pattern is formed from a photoresist composition comprising: a polymer comprising acid labile groups; and a photoacid generator;
(c) coating a pattern trimming composition of claim 1 over the photoresist pattern;
(d) heating the coated photoresist pattern; and
(e) rinsing the coated and heated photoresist pattern with a rinsing agent to remove residual pattern treatment composition.

9. The method of claim 8, wherein the rinsing agent is an aqueous tetramethylammonium hydroxide solution.

10. The method of claim 8, wherein the photoresist pattern is formed by deep-UV or EUV lithography.

11. The method of claim 8, wherein the aromatic sulfonic acid is of general formula II:

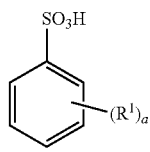

(II)

wherein: $R^1$ independently represents a fluorine atom or trifluoromethyl, and wherein an $R^1$ represents trifluoromethyl; and a represents an integer of from 2 to 5.

12. The method of claim 8, wherein the polymer comprises a repeat unit formed from a vinyl aromatic monomer.

13. The method of claim 8, wherein the organic-based solvent comprises a monoether.

14. The method of claim 13, wherein the organic-based solvent further comprises an alcohol and/or an ester.

15. The method of claim 8, wherein the composition is free of polymeric acids and polymeric acid generators.

16. The method of claim 8, wherein a first $R^1$ represents trifluoromethyl and a second $R^1$ represents a fluorine atom.

* * * * *